(12) United States Patent
Jin et al.

(10) Patent No.: US 8,507,287 B2
(45) Date of Patent: Aug. 13, 2013

(54) MESOPOROUS METAL OXIDE MATERIALS FOR PHOSPHOPROTEOMICS

(75) Inventors: Song Jin, Madison, WI (US); Ying Ge, Madison, WI (US); Cory Alexander Nelson, Madison, WI (US); Qingge Xu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 78 days.

(21) Appl. No.: 12/557,906

(22) Filed: Sep. 11, 2009

(65) Prior Publication Data

US 2010/0093102 A1    Apr. 15, 2010

Related U.S. Application Data

(60) Provisional application No. 61/100,324, filed on Sep. 26, 2008.

(51) Int. Cl.
  *G01N 33/00*    (2006.01)
(52) U.S. Cl.
  USPC ............................................. 436/86; 436/161
(58) Field of Classification Search
  USPC ............................................. 436/83, 86, 161
  See application file for complete search history.

(56) References Cited

U.S. PATENT DOCUMENTS

| | | | |
|---|---|---|---|
| 5,904,663 | A | 5/1999 | Braverman et al. |
| 6,242,581 | B1 | 6/2001 | Nelson et al. |
| 6,521,246 | B2 | 2/2003 | Sapieszko et al. |
| 6,531,523 | B1 | 3/2003 | Davankov et al. |
| 6,582,811 | B1 | 6/2003 | Davankov et al. |
| 6,592,764 | B1 | 7/2003 | Stucky et al. |
| 6,645,626 | B2 | 11/2003 | Garcia et al. |
| 6,703,498 | B2 | 3/2004 | Tchaga |

(Continued)

FOREIGN PATENT DOCUMENTS

| | | |
|---|---|---|
| EP | 1 764 147 | 3/2007 |
| WO | WO 99/37705 | 7/1999 |

(Continued)

OTHER PUBLICATIONS

In Situ Enrichment of Phosphopeptides on MALDI Plates Functionalized by Reactive Landing of Zirconium(IV)-n-Propoxide Ions Grady Blacken, Michael Volny, Tomas Vaisar, Martin Sadilek, and Frantisek Turecek Anal. Chem. Jul. 15, 2007; 79(14): 5449-5456.*

(Continued)

*Primary Examiner* — Vickie Kim
*Assistant Examiner* — Dwan A Gerido
(74) *Attorney, Agent, or Firm* — Lathrop & Gage LLP

(57) ABSTRACT

The present invention provides methods and materials for isolating, purifying, and/or enriching the concentration of compounds having one or more phosphate groups and/or derivatives thereof, including but not limited to phosphorylated peptides and/or phosphorylated proteins. In some aspects, the present invention provides nanostructured enrichment materials, such as metal oxide mesoporous materials, that selectively and reversibly bind with phosphorylated compounds with high specificity and are capable of controlled release of phosphorylated compounds bound to their active surfaces. Mesoporous materials of the present invention also provide enrichment materials having large active surface areas that provide for higher loading capacities for phosphorylated peptides and proteins relative to conventional affinity based methods. Nanostructured metal oxide mesoporous enrichment materials of the present invention are also compatible with implementation via a variety of separation platforms including flow through separation systems, elution based separation systems, column chromatography and affinity chromatography.

24 Claims, 14 Drawing Sheets

(56) References Cited

U.S. PATENT DOCUMENTS

| | | | |
|---|---|---|---|
| 6,989,254 B2 | 1/2006 | Wei et al. | |
| 7,037,425 B2 | 5/2006 | Lee et al. | |
| 7,223,377 B2 | 5/2007 | Domen et al. | |
| 7,258,981 B2 | 8/2007 | Turpin et al. | |
| 7,282,259 B2 | 10/2007 | Ku et al. | |
| 2004/0005352 A1 | 1/2004 | Lopez et al. | |
| 2004/0106178 A1 | 6/2004 | Acherman et al. | |
| 2005/0123465 A1 | 6/2005 | Chane-Ching | |
| 2005/0201917 A1 | 9/2005 | Chane-Ching | |
| 2005/0266227 A1 | 12/2005 | Ku et al. | |
| 2006/0014234 A1 | 1/2006 | Tepe et al. | |
| 2007/0071787 A1 | 3/2007 | Saffie et al. | |
| 2007/0148044 A1 | 6/2007 | Murata | |
| 2007/0227351 A1 | 10/2007 | Garcia-Martinez | |
| 2007/0281854 A1 | 12/2007 | Harbour et al. | |
| 2010/0012832 A1* | 1/2010 | Ishihama | 250/282 |

FOREIGN PATENT DOCUMENTS

| | | |
|---|---|---|
| WO | WO 99/39822 | 8/1999 |
| WO | WO 99/57992 | 11/1999 |
| WO | WO 02/25288 | 3/2002 |
| WO | WO 02/068454 | 9/2002 |
| WO | WO 03/070662 | 8/2003 |
| WO | WO 2004/013062 | 2/2004 |
| WO | WO 2004/074211 | 9/2004 |
| WO | WO 2005/044448 | 5/2005 |
| WO | WO 2005/082277 | 9/2005 |
| WO | WO 2005/110592 | 11/2005 |
| WO | WO 2005/123758 | 12/2005 |
| WO | WO 2006/004557 | 1/2006 |
| WO | WO 2006/005931 | 1/2006 |
| WO | WO 2006/106493 | 10/2006 |
| WO | WO 2006/132294 | 12/2006 |
| WO | WO 2007/053594 | 5/2007 |
| WO | WO 2007/067539 | 6/2007 |
| WO | WO 2007/092227 | 8/2007 |

OTHER PUBLICATIONS

Aebersold et al. (Web Release Jan. 23, 2001) "Mass Spectrometry in Proteomics," *Chem. Rev.* 101:269-295.

Aebersold et al. (Mar. 13, 2003) "Mass Spectrometry-Based Proteomics," *Nature* 422:198-207.

Bodenmiller et al. (Web Release Feb. 11, 2007) "Reproducible Isolation of Distinct, Overlapping Segments of the Phosphoproteome," *Nat. Methods* 4:231-237.

Breuker et al. (Oct. 20, 2003) "Native Electron Capture Dissociation for the Structural Characterization of Noncovalent Interactions in Native Cytochrome C," *Angew. Chem. Int. Ed.* 42(40):4900-4904.

Brinker et al. (May 1999) "Evaporation-Induced Self-Assembly: Nanostructures Made Easy," *Adv. Mater.* 11(7):579-585.

Carr et al. (Aug. 1, 1996) "Selective Detection and Sequencing of Phosphopeptides at the Femtomole Level by Mass Spectrometry," *Anal. Biochem.* 239(2):180-192.

Chait, B.T. (Oct. 6, 2006) "Mass Spectrometry: Bottom-up or Top-Down," *Science* 314:65-66.

Chen et al. (2008) "Trapping Performance of $Fe_3O_4$@$Al_2O_3$ and $Fe_4O_4$@$TiO_2$ Magnetic Nanoparticles in the Selective Enrichment of Phosphopeptides from Human Serum," *J. Biomed. Nanotechnol.* 4(1):73-79.

Chen et al. (Sep. 15, 2005) "$Fe_3O_4$/$TiO_2$ Core/Shell Nanoparticles as Affinity Probes for the Analysis of Phosphopeptides Using $TiO_2$ Surface-Assisted Laser Desorption/Ionization Mass Spectrometry," *Anal. Chem.* 77(18):5912-5919.

Clontech (2010) "Magnetic Phosphopeptide Enrichment Kit," http://www.clontech.com/products/detail.asp?product_id=167163&tabno=2.

Cooper et al. (Mar./Apr. 2005) "The Role of Electron Capture Dissociation in Biomolecular Analysis," *Mass Spec. Rev.* 24(2):201-222.

Cuccurullo et al. (Aug. 1, 2007) "Identification of Phosphoproteins and Determination of Phosphorylation Sites by Zirconium Dioxide Enrichment and SELDI-MS/MS," *J. Mass. Spec.*42(8):1069-1078.

Fan et al. (Web Release Dec. 19, 2006) "Nanoparticle Assembly of Ordered Multicomponent Mesostructured Metal Oxides via a Versatile Sol-Gel Process," *Chem. Mater.* 18(26):6391-6396.

Ficarro et al. (Web Release May 21, 2008) "Niobium(V) Oxide ($Nb_2O_5$): Application to Phosphoproteomics," *Anal. Chem.* 80(12):4606-4613.

Ficarro et al. (Mar. 2002) "Phosphoproteome Analysis by Mass Spectrometry and its Application to *Saccharomyces cerevisiae*," *Nat. Biotechnol.* 20:301-305.

Ge et al. (Web Release Jan. 5, 2002) "Top Down Characterization of Larger Proteins (45 kDa) by Electron Capture Dissociation Mass Spectrometry," *J. Am. Chem. Soc.* 124(4):672-678.

Ge et al. (Aug. 4, 2009) "Top-Down High-Resolution Mass Spectrometry of Cardiac Myosin Binding Protein C Revealed That Truncation Alters Protein Phosphorylation State," *Proc. Nat. Acad. Sci. USA* 106(31):12658-12663.

Ge et al. (Mar. 2003) "Top Down Characterization of Secreted Proteins from *Mycobacterium tuberculosis* by Electron Capture Dissociation Mass Spectrometry," *J. Am. Soc. Mass Spectrom.* 14(3):253-261.

Glygen et al. "Trap Columns," http://www.glygen.com/index.php?option=com_content&view=article&id=60&Itemid=95 , Downloaded Feb. 5, 2010.

Glygen "TopTip and Spin Column-in-a-Tip," http://www.glygen.com/index.php?option=com_content&view=article&id=45&Itemid=93 , Downloaded Feb. 5, 2010.

Glygen "NuTip," http://www.glygen.com/index.php?option=com_content&view=article&id=44&Itemid=104 , Downloaded Feb. 5, 2010.

Goshe et al. (Web Release Apr. 28, 2001) "Phosphoprotein Isotope-Coded Affinity Tag Approach for Isolating and Quantitating Phosphopeptides in Proteome-Wide Analyses," *Anal. Chem.* 73(11):2578-2586.

Han et al. (Feb. 15, 2008) "Mesoporous $Fe_2O_3$ Microspheres: Rapid and Effective Enrichment of Phosphopeptides for MALDI-TOF MS Analysis," *J. Colloid. Interface Sci.* 318(2):315-321.

Han et al. (2008) "Development of Phosphopeptide Enrichment Techniques for Phosphoproteome Analysis," *Analyst* 133:1128-1138.

Hsieh et al. (Web Release Aug. 9, 2007) "Development of Titanium Dioxide Nanoparticles Pipette-Tip for the Selective Enrichment of Phosphorylated Peptides," *J. Chromatogr. A* 1165:128-135.

Huang et al. (Sep. 26, 2008) "Phosphoproteomics: Unraveling the Signaling Web," *Mol. Cell* 31:777-781.

Hunter, T. (Jan. 7, 2000) "Signaling—200 and Beyond," *Cell* 100:113-127.

International Search Report and Written Opinion, Corresponding to International Application No. PCT/US2009/056632, Mailed Oct. 28, 2009.

Jumaa et al. (Apr. 2005) "B Cell Signaling and Tumorigenesis," *Ann. Rev. Immunol.* 23:415-445.

Kisler et al. (2001) "Separation of Biological Molecules Using Mesoporous Molecular Sieves," *Microporous Mesoporous Mater.* 44-45:769-774.

Kjeldsen et al. (Web Release Jun. 13, 2007) "On Studying Protein Phosphorylation Patterns Using Bottom-Up LC-MS/MS: The Case of Human α-Casein," *Analyst* 132:768-776.

Kresge et al. (Oct. 22, 1992) "Ordered Mesoporous Molecular Sieves Synthesized by a Liquid-Crystal Template Mechanism," *Nature* 359:710-712.

Kweon et al. (Feb. 7, 2006) "Selective Zirconium Dioxide-Based Enrichment of Phosphorylated Peptides for Mass Spectrometric Analysis," *Anal. Chem.* 78(6):1743-1749.

Larsen et al. (Apr. 27, 2005) "Highly Selective Enrichment of Phosphortylated Peptides from Peptide Mixtures Using Titanium Dioxide Microcolumns," *Mol. Cell. Proteomics* 4:873-886.

Lo et al. (Web Release Dec. 22, 2006) "Rapid Enrichment of Phosphopeptides from Tryptic Digests of Proteins Using Iron Oxide Nanocomposites of Magnetic Particles Coated with Zirconia as the Concentrating Probes," *J. Proteome Res.* 6:887-893.

Lu et al. (Sep. 25, 1997) "Continuous Formation of Supported Cubic and Hexagonal Mesoporous Films by Sol-Gel Dip-Coating," *Nature* 389:364-368.

Mann et al. (2001) "Analysis of Proteins and Proteomics by Mass Spectrometry," *Ann. Rev. Biochem.* 70:437-473.

Mann et al. (Jun. 1, 2002) "Analysis of Protein Phosphorylation Using Mass Spectrometry: Deciphering the Phosphoproteome," *Trends Biotechnol.* 20(6):261-268.

McLachlin et al. (Oct. 1, 2001) "Analysis of Phosphorylated Proteins and Peptides by Mass Spectrometry," *Curr. Opin. Chem. Biol.* 5(5):591-602.

McLafferty, et al. (May 21, 1999) "Biomolecule Mass Spectrometry," *Science* 284:1289-1290.

Nawrocki et al. (Dec. 31, 1993) "Chemistry of Zirconia and its Use in Chromatography," *J. Chromatogr.* A 657(2):229-282.

Nelson et al. (2009) "Mesopourous Zirconium Oxide Nanomaterials Effectively Enrich Phosphopeptides for Mass Spectrometry-Based Phosphoproteomics," *Chem. Commun.* :6607-6609.

New Objective (2004) "Sample Prep and Injection Essentials," http://www.newobjective.com/products/ess_samplesprep.html.

Oda et al. (Apr. 2001) "Enrichment Analysis of Phosphorylated Proteins as a Tool for Probing the Phosphoproteome," *Nat. Biotechnol.* 19: 379-382.

Pandey et al. (Jun. 15, 2000) "Proteomics to Study Genes and Genomes," *Nature* 405:837-846.

Pawson et al. (Apr. 18, 2003) "Assembly of Cell Regulatory Systems Through Protein Interaction Domains," *Science* 300:445-452.

Perkin Elmer "Phos-Trap," Perkin Elmer Catalog, http://las.perkinelmer.com/Catalog/FamilyPage.htm?CategoryID=Phos-Trap , Downloaded Feb. 5, 2010.

Pinkse et al. (Web Release Jun. 15, 2004) "Selective Isolation at the Femtomole Level of Phosphopeptides from Proteolytic Digests Using 2D-NanoLC-ESI-MS/MS and Titanium Oxide Precolumns," *Anal. Chem.* 76(14):3935-3943.

Porath et al. (Dec. 18, 1975) "Metal Chelate Affinity Chromatography, A New Approach to Protein Fractionation," *Nature* 258:598-599.

Posewitz et al. (Jul. 15, 1999) "Immobilized Gallium(III) Affinity Chromatography of Phosphopeptides," *Anal. Chem.* 71(14):2883-2892.

Rai et al. (Nov. 2001) "Hydroxo and Chloro Complexes/Ion Interactions of $Hf4+$ and the Solubility Product of HfO29am)," *J. Solution Chem.* 30(11):949-967.

Salih, E. (Nov./Dec. 2005) "Phosphoproteomics by Mass Spectrometry and Classical Protein Chemistry Approaches," *Mass Spec. Rev.* 24(6):828-846.

Schüth et al. (Web Release Jul. 10, 2001) "Non-Siliceous Mesostructured and Mesoporous Materials," *Chem. Mater.* 13:3184-3195.

Senko et al. (Sep. 1994) "Collisional Activation of Large Multiply Charged Ions Using Fourier Transform Mass Spectrometry," *Anal. Chem.* 66(18):2801-2808.

Shi et al. (Web Release Nov. 30, 2000) "Phosphopeptide/Phosphoprotein Mapping by Electron Capture Dissociation Mass Spectrometry," *Anal. Chem.* 73(1):19-22.

Steen et al. (2006) "Phosphorylation Analysis by Mass Spectroscopy," *Mol. Cell. Proteomics* 5(1):172-181.

Swiss-Prot Protein Knowledgebase TrEMBL Computer-Annotated Supplement to Swiss-Prot, http://www.expasy.ch/sprot/, Last modified Jan. 19, 2010.

Sze et al. (Feb. 19, 2002) "Top-Down Mass Spectrometry of a 29-kDa Protein for Characterization of any Posttranslational Modification to Within One Residue," *Proc. Nat. Acad. Sci. USA* 99(4):1774-1779.

Tan et al. (2007) "Specific Capture of Phosphopeptides on Matrix-Assisted Laser Desorption/Ionization Time-of-Flight Mass Spectrometry Targets Modified by Magnetic Affinity Nanoparticles," *Rapid Commun. Mass Spectrom.*21:2407-2414.

Tao et al. (Aug. 2005) "Quantitative Phosphoproteome Analysis Using a Dendrimer Conjugation Chemistry and Tandem Mass Spectrometry," *Nat. Methods* 2(8):591-598.

Thingholm et al. (Web Release Nov. 22, 2006) "Highly Selective Enrichment of Phosphorylated Peptides Using Titanium Dioxide," *Nat. Protocols* 1(4):1929-1935.

Tian et al. (2002) "Fast Preparation of Highly Ordered Nonsiliceous Mesoporous Materials via Mixed Inorganic Precursors," *Chem. Comm.* 17:1824-1825.

Wang et al. (Mar. 19-20, 2007) "Enrichment and Characterization of Histone H1 Phosphorylation Isoforms in Chemoprevention of Acute Myeloid Leukemia," *4th Annual Ohio Mass Spectrometry Symposium* pp. 44-45.

Wolf-Yadlin et al. (Apr. 3, 2007) "Multiple Reaction Monitoring for Robust Quantitative Proteomic Analysis of Cellular Signaling Networks," *Proc. Natl. Acad. Sci. U.S.A.* 104(14):5860-5865.

Wolters et al. (Dec. 1, 2001) "An Automated Multidimensional Protein Identification Technology for Shotgun Proteomics," *Anal. Chem.* 73:5683-5690.

Yang et al. (Web Release Sep. 29, 1999) "Block Copolymer Templating Syntheses of Mesoporous Metal Ociedes with Large Ordering Lengths and Semicrystalline Framework," *Chem. Mater.* 11(10):2813-2826.

Yang et al. (Nov. 12, 1998) "Generalized Synthesis of Large-Pore Mesoporous Metal Oxides with Semicrystalline Framework," *Nature* 396:152-155.

Yates, J.R. (1998) "Mass Spectrometry and the Age of the Proteome," *J. Mass Spectrom.* 33:1-19.

Yuan et al. (Feb. 4, 2005) "Preparation of Highly Ordered Mesoporous $WO_3$-$TiO_2$ as Matrix in Matrix-Assisted Laser Desorption/Ionization Mass Spectrometry," *Microporous Mesoporous Mater.* 78(1):37-41.

Zabrouskov et al (2008) "Unraveling Molecular Complexity of Phosphorylated Human Cardiac Troponin I by Top Down Electron Capture Dissociation/Electron Transfer Dissociation Mass Spectrometry," *Mol. Cell. Proteom.* 7(10):1838-1849.

Zhang et al. (2007) ,,Highly Efficient Phosphopeptide Enrichment by Calcium Phosphate Precipitation Combined with Subsequent IMAC Enrichment, *Mol. Cell. Proteomics* 6(11):2032-2042.

Zhou et al. (Apr. 2001) "A Systematic Approach to the Analysis of Protein Phosphorylation," *Nat. Biotechnol.* 19:375-378.

Zhou et al. (Jul. 1, 2007) "Highly Specific Enrichment of Phsphopeptides by Zirconium Dioxide Nanoparticles for Phosphoproteome Analysis," *Electrophoresis* 28(13):2201-2215.

Zhu et al. (Feb. 2007) "Using Titanium Dioxide IMAC for Enrichment of Phosphopeptides Prior to Tandem Mass Spectrometry," *J. Biomol. Techniques* 18(1):24-25, ABRF-07.

Zubarev et al. (Web Release Mar. 24, 1998) "Electron Capture Dissociation of Multiply Charges Protein Cations. A Nonergodic Process," *J. Am. Chem. Soc.* 120(13):3265-3266.

Zubarev et al. (Web Release Jan. 5, 2000) ,,Electron Capture Dissociation for Structural Characterization of Multiply Charges Protein Cations, *Anal. Chem.* 72(3):563-573.

Burleigh et al. (Nov. 15, 2003) "A Versatile Synthetic Approach to Periodic Mesopourous Organosilicas," *Colloid Polym Sci* 282:728-33.

Chadhari and Kumar (Jan. 26, 2005) "Intercalations of Proteins into α-Zirconium Phosphonates: Tuning the Phosphate Affinities with Phosphonate Functions," *Micropor Mesopor Mat* 77(2-3):175-87.

Feng et al. (Jun. 17, 2007) "Immobilized Zirconium Ion Affinity Chromatography for Specific Enrichment of Phosphopeptides in Phosphoproteome Analysis," *Mol Cell Proteomics* 6(9):1656-65.

Haskouri et al. (2004) "The First Pure Mesoporous Aluminium Phosphonates and Diphosphonates—New Hybrid Porous Materials," *Eur J Inorg Chem* 2004:1804-07.

Imanishi et al. (May 17, 2007) "Reference-Facilitated Phosphoproteomics: Fast and Reliable Phosphopeptide Validation by μLC-ESI-Q-TOP MS/MS," *Mol Cell Proteomics* 6(8):1380-91.

Sayari and Hamoudi (2001) "Periodic Mesoporous Silica-Based Organic-Inorganic Nanocomposite Materials," *Chem Mater* 13:3151-68.

Schuth (2001) "Non-siliceous Mesostructured and Mesoporous Materials," *Chem Mater* 13:3184-95.

Stein et al. (Oct. 2, 2000) "Hybrid Inorganic-Organic Mesoporous Silicates—Nanoscopic Reactors Coming of Age," *Adv Mater* 12(19):1403-19.

Nelson et al. (Aug. 12, 2010) "Effective Enrichment and Mass Spectrometry Analysis of Phosphopeptides Using mesoporous Metal Oxide Nanomaterials," *Anal. Chem.*, 82:7193-7201.

* cited by examiner

MESOPOROUS METAL OXIDE MATERIALS FOR PHOSPHOPROTEOMICS

CROSS REFERENCE TO RELATED APPLICATION

This application claims the benefit of U.S. provisional application 61/100,324 filed Sep. 26, 2008, which is incorporated by reference in its entirety herein to the extent not inconsistent with the disclosure herein.

STATEMENT REGARDING FEDERALLY SPONSORED RESEARCH OR DEVELOPMENT

Not applicable.

BACKGROUND OF THE INVENTION

Proteins are involved in nearly every aspect of cellular function; therefore technologies for global protein characterization are necessary to virtually all areas of the biological sciences. Research in the field of proteomics has expanded tremendously over the last decade due to its potential to revolutionize biological and medical research, particularly for the development of new drugs, therapies and diagnostic methods. The term proteome is used to describe the entire set of proteins encoded by a genome. In a broader sense, however, the study of the proteome, referred to generally as the field of proteomics, involves the characterization of gene and cellular function by determining the identities, activities, interactions, localization and modifications of individual proteins and protein complexes present in a cell or tissue. Technology development has, and continues, to drive rapid evolution in this field.

Research has demonstrated that a proteome is typically characterized by very dynamic behavior. For example, the types of proteins expressed by a cell, as well as their abundances, post-translational modifications and subcellular locations, vary substantially with the physiological condition of a cell or tissue, including the onset and progression of disease. Accordingly, quantitative characterization of changes in protein content, composition and activity at the organ, tissue, and cellular levels provide information useful for identifying new biological targets for drug development and novel biomarkers for the diagnosis and early detection of disease. Furthermore, proteomics research is highly complementary to other functional approaches for understanding cellular and sub-cellular processes, such as microarray-based expression profiles, systems level genetics, and small molecule based arrays.

The complexity of proteomics, at least in part, is due to the large number of proteins and protein complexes corresponding to a genome. For example, the human proteome is expected to consist of between about 400,000 to about 1,000,000 proteins, which interact to form a huge number of protein-protein complexes important in regulating cellular behavior. The complexity of the human proteome is significantly compounded by the large dynamic range observed for protein expression, typically exceeding over six orders of magnitude, and by post-translational modifications that critically impact protein activity and function. To address this inherent complexity, a number of high throughput platforms for identifying and characterizing proteins have been developed, including two-dimensional gel electrophoresis (2D-GE) protein identification methods, genetic readout experiments, such as the yeast two-hybrid assay, micro-array and chip technologies, and mass spectrometry methods.

Mass spectrometry has emerged as a preferred experimental tool for proteomics given its sensitivity, speed, versatility and specificity. [McLafferty, F. W.; Fridriksson, E. K.; Horn, D. M.; Lewis, M. A.; Zubarev, R. A., *Science* 1999, 284, 1289-1290]. In addition, mass spectrometric analysis is well suited for automated, high throughput operation, particularly when combined with multidimensional separation techniques, such as high performance liquid chromatography (HPLC) or capillary electrophoresis. As a result significant research has been directed toward developing mass spectrometry-based techniques for identifying proteins in complex mixtures, probing protein-protein interactions and characterizing post-translational modifications. The application of mass spectrometric methods to protein identification has been the subject of numerous scientific publications including "Mass Spectrometry and the Age of the Proteome," Yates, J. R., *J. Mass Spectrometry*, Vol 33, 1-19 (1998); "Mass Spectrometry-based Proteomics," Aebersold, R., Mann, Matthias, *Nature*, 2003, 198-207; "Proteomics to Study Genes and Genomes," Pandey, A. and Mann, M., *Nature*, 2000, 405, 837-846; "Mass Spectrometry in Proteomics," Aebersold, R. and Goodlett, D. R., *Chem. Rev., Vol* 101, 269-295 (2001); "An automated Multidimensional Protein Identification Technology for Shotgun Proteomics," Wolters, D. A., Washburn, M. P. and Yates, J. R., III, *Anal Chem.*, Vol 73, 5683-5690 (2001); and "Analysis of Proteins and Proteomes by Mass Spectrometry," Mann, M., Hendrickson, R. C. and Pandey, A., *Annu. Rev, Biochem, Vol.* 70, 437-473 (2001), which are all hereby incorporated by reference in their entireties to the extent not inconsistent with the present description.

Traditionally, protein sequences are determined by stepwise enzymatic degradation of purified proteins into peptide fragments, for example by trypsin digestion, subsequent analysis of the peptide fragments by mass spectrometry and protein/peptide characterization using advanced bioinformatic tools. Recent interest has focused on the characterization of proteins with complex post-translational modifications, as these modifications are known to play a critical role in the function and regulation of proteins. [Ge, Y.; Lawhorn, B. G.; ElNaggar, M.; Strauss, E.; Park, J. H.; Begley, T. P.; McLafferty, F. W., *J. Am. Chem. Soc.* 2002, 124, 672-678. Ge, Y.; ElNaggar, M.; Sze, S. K.; Bin Oh, H.; Begley, T. P.; McLafferty, F. W.; Boshoff, H.; Barry, C. E., *J. Am. Soc. Mass Spectrom.* 2003, 14, 253-261. Sze, S. K.; Ge, Y.; Oh, H.; McLafferty, F. W., *Proc. Nat'l Acad. Sci. USA* 2002, 99, 1774-1779.]. Reversible protein phosphorylation, for example, is a ubiquitous post-translational modification involved in many biological processes, including cell growth, division, and signaling. [Hunter, T., *Cell* 2000, 100, 113-127]. In addition, aberrant protein phosphorylation is indentified as responsible for many human diseases, including cancer and heart diseases. As a result of the well recognized importance of protein phosphorylation, considerable proteomic research is directed to the identification of phosphorylation states and specific phosphorylation sites of phosphoproteins/phosphopeptides.

Advanced mass spectrometry methodologies have been developed enabling selective identification and characterization of the phosphorylation state of single proteins or peptides (See. e.g. Shi, S. D. H.; Hemling, M. E.; Carr, S. A.; Horn, D. M.; Lindh, I.; McLafferty, F. W., *Anal. Chem.* 2001, 73, 19-22; Carr, S. A.; Huddleston, M. J.; Annan, R. S., *Anal. Biochem.* 1996, 239, 180-192; Kjeldsen, F.; Savitski, M. M.; Nielsen, M. L.; Shi, L.; Zubarev, R. A., *Analyst* 2007, 132, 768-776; Steen, H.; Jebanathirajah, J. A.; Rush, J.; Morrice, N.; Kirschner, M. W., *Mol. Cell. Proteomics* 2006, 5, 172-181. Zabrouskov, V.; Ge, Y.; Schwartz, J.; Walker, J. W., *Mol.*

Cell. Proteomics 2008, 7, 1838-1849. Ge, Y.; Rybakova, I.; Xu, Q.; Moss, R. L. Proc. Natl. Acad. Sci. U.S.A. 2009, 106, 12658-12663.). Implementation of these techniques, however, presents significant challenges given the low abundance of phosphoproteins and substoichiometric phosphorylation commonly observed in many biological environments. To realize the benefits provided by mass spectrometry-based methods for proteomics, therefore, techniques for purifying and enriching phosphoproteins and phosphopeptides are currently needed. A number of either affinity- or chemical derivatization-based purification and enrichment techniques have attracted attention recently to complement mass spectrometry based proteomics analysis of phosphorylated proteins and peptides [See, e.g., "Reproducible isolation of distinct, overlapping segments of the phosphoproteome," Bodenmeiller, B., Mueller, L. N., Mueller, M., Domon, B., Aebersold, R., Nature Methods, 2007, 4, 231-237; "Quantitative phosphoproteome analysis using a dendrimer conjugation chemistry and tandem mass spectrometry"; Tao, W. A., Wollscheid, B., O'Brien, R., Eng, J. K., Li, X. J., Bodenmiller, B., Watts, J. D., Hood, L. and Aebersold, R., Nature Methods, 2005, 591-598; and "Enrichment analysis of phosphorylated proteins as a tool for probing the phosphoproteome"; Oda, Y., Nagasu, T. and Chait, B. T., Nature Biotechnol., 2001, 379-382, which are all hereby incorporated by reference in their entireties to the extent not inconsistent with the present description].

In contrast to the chemical derivatization-based method which suffers from side reaction, increased sample complexity and potential loss of phosphate, the affinity based method is more commonly used. Affinity based methods for phosphopeptide enrichment using immobilized metal ion affinity chromatography (IMAC) are well developed for mass spectrometry-based proteomic analysis. [See, e.g., Porath, J.; Carlsson, J.; Olsson, I.; Belfrage, G., Nature 1975, 258, 598-599; and Zhang, X.; Ye, J. Y.; Jensen, O. N.; Roepstorff, P., Mol. Cell. Proteomics 2007, 6, 2032-2042, which are all hereby incorporated by reference in their entireties to the extent not inconsistent with the present description]. Conventional techniques include use of metal ions, such as Ga(III) and Fe(III), that provide specific and reversible chemisorption of phosphate groups of phosphoproteins and phosphopeptides. Such metal ion affinity materials, however, are known to also bind to certain non-phosphorylated amino acid residues, such as glutamic and aspartic acid, degrading overall specificity. An alternate approach uses metal oxide materials for affinity based enrichment of phosphopeptides. $TiO_2$ and $ZrO_2$, metal oxides, for example, have been pursued and are believed to exhibit less non-specific binding and higher specificity for trapping phosphates as compared to conventional metal ion affinity materials. [See, e.g., Pinkse, M. W. H.; Uitto, P. M.; Hilhorst, M. J.; Ooms, B.; Heck, A. J. R., Anal. Chem. 2004, 76, 3935-3943. Kweon, H. K.; Hakansson, K., Anal. Chem. 2006, 78, 1743-1749]. Nanoparticle metal ion and metal oxide materials have also been explored due to their expected higher capacities than microparticles. [See, e.g., Chen, C. T.; Chen, Y. C., J. Biomed. Nanotechnol. 2008, 4, 73-79; Zhou, H. J.; Tian, R. J.; Ye, M. L.; Xu, S. Y.; Feng, S.; Pan, C. S.; Jiang, X. G.; Li, X.; Zou, H. F., Electrophoresis 2007, 28, 2201-2215].

U.S. Patent Application Publication No. 2006/0014234, published on Jan. 19, 2006, discloses a chemical derivatization-based method for the enrichment and separation of phosphorylated peptides or proteins. Techniques disclosed in this reference include the use of an organo-functionalized separation medium for enriching phosphorylated peptides and proteins present in complex mixtures. Separation media functionalized with diazo moieties linked by an organic group are reported as particularly useful for mass spectrometry based characterization of phosphopeptides. This reference further discloses enrichment processes involving protection of carboxylate groups to reduce interferences with selective immobilization of phosphorylated peptides. A wide range of organo-functionalized separation materials are disclosed in this reference including resins, polymers, metal oxides, metal hydroxides, mesoporous materials, metals, silicate clays, and metal phosphates.

It will be appreciated from the foregoing that there is currently a need for improved methods and materials for identifying and analyzing phosphorylated peptides and proteins.

SUMMARY OF THE INVENTION

The present invention provides methods and materials for isolating, purifying, and/or enriching the concentration of compounds having one or more phosphate groups and/or derivatives thereof, including but not limited to phosphorylated peptides and/or phosphorylated proteins. In some aspects, the present invention provides nanostructured enrichment materials, such as metal oxide mesoporous materials including transition metal oxide and/or Group IIIA metal oxide mesoporous materials that selectively and reversibly bind with phosphorylated compounds with high specificity and are capable of controlled release of phosphorylated compounds bound to their active surfaces. Mesoporous materials of some aspects have a well-ordered nano-pore structure providing enrichment materials exhibiting large active areas of exposed surfaces (e.g., greater than or equal to 50 $m^2$ $g^{-1}$) resulting in higher loading capacities for phosphorylated peptides and proteins relative to conventional affinity based methods. Nanostructured metal oxide mesoporous enrichment materials of some of the present methods are also compatible with implementation via a variety of separation platforms including flow through separation systems, elution based separation systems, column chromatography and affinity chromatography.

The methods and nanostructured enrichment materials of the present invention are highly versatile and, thus applicable for enrichment, purification and analysis of phosphorylated compounds in a range of samples, including biological samples derived from living cells and tissue. The large active surface areas of mesoporous materials of the present invention make these methods particularly attractive for enrichment of phosphorylated protein and/or peptide component(s) present over a wide range of concentrations including very low concentrations. In addition, the high degree of selectivity of metal oxide mesoporous materials for phosphorylated compounds, particularly phosphopeptides and phosphoproteins, provides separation media useful for purifying, enriching and analyzing the components of complex mixtures. Methods and nanostructured materials of the present invention are highly complementary to mass spectrometric-based methods for the identification, analysis and characterization of phosphorylated proteins and peptides, and derivatives thereof. Methods of the present invention, for example, may be useful for generating samples enriched in one or more phosphorylated protein or peptide components for subsequent mass spectrometric analysis. Methods of the present invention are useful for analyzing, sequencing and otherwise characterizing phosphorylated proteins and peptides via mass spectrometry, for example via bottom up and top down mass spectrometry-based sequencing and/or characterization techniques.

In an aspect, the present invention provides methods for enriching phosphorylated compounds provided in a sample using an enrichment material comprising a nanostructured metal oxide provided in a mesoporous state. In a specific embodiment, for example, a method of the present invention comprises the steps of: (i) providing a sample containing one or more phosphorylated compounds; (ii) contacting the sample with an enrichment material comprising a metal oxide mesoporous material, wherein at least a portion of the phosphorylated compounds selectively binds to the metal oxide mesoporous material; (iii) separating the phosphorylated compounds bound to the metal oxide mesoporous material from at least a portion of the sample; and (v) releasing the phosphorylated compounds bound to the metal oxide mesoporous material, thereby enriching the phosphorylated compounds provided in the sample. In an embodiment, at least a portion of the phosphorylated compounds directly binds to the metal oxide mesoporous enrichment material. In an embodiment, the phosphorylated compounds enriched in the sample are phosphorylated peptides and/or phosphorylated proteins, or derivatives and/or fragments thereof. In an embodiment, the enrichment material comprises a transition metal oxide mesoporous material, a Group IIIA metal oxide mesoporous material or a combination of both. In an embodiment, the separating step is carried out after the contacting step, and the releasing step is carried out after the separating step. In an embodiment, the enrichment material comprises a metal oxide mesoporous material having a plurality of pores with cross sectional dimensions (e.g., diameter, radius, width, thickness, etc.) selected over the range of 2 to 50 nanometers. In an embodiment, the enrichment material comprises a metal oxide mesoporous material having a surface area selected over the range 50 to 1000 m² per gram. In an embodiment, the enrichment material comprises particles of the metal oxide mesoporous material having cross sectional dimensions ranging from 50 nanometers to 2 millimeters.

Enrichment materials useful in the present invention comprise nanostructured mesoporous metal oxides including transition metal oxides, Group 1 metal oxides, Group 2 metal oxides, Group IIIA metal oxides and lanthanide metal oxides. As used herein, the term "mesoporous" refers to porous materials characterized by a plurality of pores with cross sectional dimensions (e.g., diameter or width) selected over the range of 2 to 50 nm, optionally provided in a well ordered network. Optionally, mesoporous metal oxide materials of the present invention have pores with cross sectional dimensions selected over the range of 4 to 20 nm. The extensive pore structure of mesoporous materials of the present invention provide extremely large surface areas ranging from 50 to 1000 m² g⁻¹. Mesoporous enrichment materials of the present invention preferably have pores with cross sectional dimensions large enough to allow efficient transport of phosphorylated compounds, such as phosphorylated proteins and peptides, into and through the pores of the enrichment material. The various pore network structures of the present mesoporous enrichment materials, such as hexagonal and cubic biocontinuous are also beneficial for enabling flow through of the samples subject to enrichment processing.

The pore structures of the present enrichment materials provide surfaces with many reactive sites that can associatively interact (e.g., bind) with the phosphorylated compounds, thereby providing enrichment materials having large active areas and useful loading capacities. The mesoporous enrichment materials of the present invention provide active areas large enough to allow for efficient binding of phosphorylated compounds provided at very low concentrations. In the context of this description, "active area" refers to surfaces of an enrichment material exposed to a sample that can participate in associative interactions with phosphorylated compounds, such as chemical reactions and/or adsorption, physisorption and/or chemisorption processes. Associative interactions between phosphorylated compounds and the active area of enrichment materials of the present invention include van der Waals interactions, dipole-dipole interactions, columbic interactions, and covalent bonds. In some embodiments of the present invention, the active areas of enrichment materials of the present invention are not functionalized, for example, not functionalized by one or more organic groups, such as diazo groups.

Mesoporous enrichment materials of the present invention have compositions providing efficient and selective associative interaction (e.g., binding) with phosphorylated compounds, such as phosphorylated proteins and phosphorylated peptides. The term "selective" in the context of this description refers to the chemical property of the enrichment materials to bind phosphorylated compounds preferentially relative to non-phosphorylated compounds provided in a sample. Certain metal oxides are particularly useful as enrichment materials in the present methods because they preferentially and reversibly bind the phosphate group(s) in phosphorylated peptides and phosphorylated proteins. In a specific embodiment, for example, the enrichment material comprises one or more metal oxide mesoporous material(s), selected from the group consisting of $ZrO_2$, $HfO_2$, $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, and the mixed oxides between them, such as $Zr_xHf_{1-x}O_2$ (wherein 0<x<1), $Zr_xTi_{1-x}O_2$ (wherein 0<x<1), $Ti_xHf_{1-x}O_2$ (wherein 0<x<1), and $(Fe_{1-x}Ga_x)_2O_3$ (wherein 0<x<1). In a specific embodiment, for example, the enrichment material comprises one or more metal oxide mesoporous material(s), selected from the group consisting of $ZrO_2$, $HfO_2$, and $TiO_2$. In an embodiment, the enrichment material is a single metal oxide. Alternatively, the invention includes methods using an enrichment material comprising a plurality of different metal oxides, such as 2-5 different metal oxides. In an embodiment, the enrichment materials is a mixed metal oxide such as $Zr_xHf_{1-x}O_2$ (wherein 0<x<1), $Zr_xTi_{1-x}O_2$ (wherein 0<x<1), $Ti_xHf_{1-x}O_2$ (wherein 0<x<1), or $(Fe_{1-x}Ga_x)_2O_3$ (wherein 0<x<1).

Mesoporous metal oxide materials provide particularly useful enrichment materials in the present enrichment methods because they are chemically stable, mechanically robust and, in some instances, can be easily and inexpensively obtained. In some embodiments, the mesoporous metal oxide material is provided as particles having average cross sectional dimensions selected over the range of 50 nanometers to 2 millimeter, wherein the particles are optionally loaded together and packed to provide a column (e.g., minicolumn) or other chromatographic product (e.g., pipette tip-based product). In some embodiments, the mesoporous metal oxide is provided as a monolithic structure, and optionally as a monolithic column. In some embodiments, the mesoporous metal oxide is provided as a fiber, and optionally provided as a filter, such as a filter disk woven from mesoporous fibers. In an embodiment the amount of the mesoporous metal oxide provided to the sample is selected over the range of 0.001 g to 100 g per milliliter of sample solution. In some embodiments, approximately 4 mg of the mesoporous material is used for enrichment of 0.01 milliliter of sample solution. In an embodiment, the metal oxide mesoporous material of the present invention is generated via controlled hydrolysis of metal salts templated using nanoscale micellular structures. In another embodiment, metal oxide mesoporous materials of the present invention are amphoteric in character and may, for example, display acidic characteristics when provided in an acidic solution. In an embodiment, the enrichment material comprises a metal oxide mesoporous material having active areas, such as exposed surfaces, that are not modified. In some embodiments, the metal oxide mesoporous material of the enrichment material may have active areas that are not functionalized such as active areas that are not organofunctionalized. In some embodiments, for example, active areas of the present mesoporous materials are not functionalized with diazo group substituted organic moieties. In an embodiment, the enrichment material comprises a metal oxide mesoporous material having an active area of exposed surfaces that are not organofunctionalized. In an embodiment, the metal oxide mesoporous material is provided as a woven fiber.

In a specific method of this aspect, the contacting step provides at least a portion of the phosphorylated compounds in the sample, such as phosphorylated peptides or proteins, such that they associatively interact with surfaces of the metal oxide mesoporous enrichment material, for example via chemical reactions, and/or adsorption, physisorption and/or chemisorption processes. In an embodiment, the contacting step provides at least a portion of the phosphorylated compounds in physical contact with the active area of exposed surfaces of the metal oxide mesoporous material, for example the surfaces of nano-pores extending within the mesoporous materials. Contacting may be carried out in a solution phase and/or liquid phase of the sample itself, for example by providing the metal oxide mesoporous material to the sample, or a solution phase and/or liquid phase derived from the sample, for example a sample containing one or more buffers for establishing preselected solution conditions to enhance selective binding. In an embodiment, the step of contacting the sample with the enrichment material comprises mixing the sample and the mesoporous metal enrichment materials to generate a heterogeneous mixture, optionally followed by agitating, mixing, vortexing and/or centrifuging the heterogeneous mixture. In another aspect, the step of contacting the sample with the enrichment material comprises flowing the sample on, through or within the mesoporous metal enrichment materials. Optionally, the enrichment materials can be fixed, sealed, or packaged into columns, tips, and filter disks, through monolithic synthesis, packing from particles, or weaving from fibers.

Solution phase conditions during the contacting step are preferably selected in some methods to provide enhanced associative interaction between the phosphorylated compound(s) and the mesoporous metal oxide enrichment material(s) and may also be selected to reduce the occurrence of non-specific binding of non-phosphorylated compounds to surfaces of the enrichment material(s). For example, selection of solution phase conditions, such as pH, ionic strength and temperature, and solution phase composition is useful in some aspects for enhancing the selectivity and/or strength of associative interaction between the phosphorylated compound(s) and the mesoporous metal oxide enrichment materials. In an embodiment useful for enriching phosphorylated proteins and/or peptides, the contacting step is carried out under acidic conditions, for example, at a pH selected over the range of 1.5 to 5, and optionally at a pH selected over the range of 1.5 to 3. Acidic solution conditions for the contacting steps is beneficial for reducing the occurrence of non-specific bonding of non-phosphorylated proteins and/or peptides with surfaces of the mesoporous metal oxide enrichment materials. In an embodiment useful for enriching phosphorylated proteins and/or peptides, for example, the contacting step is carried out in the presence of one or more additives, such as buffers and/or binding agents, for example additives selected from the group consisting of: phthalic acid, trifluoroacetic acid (TFA), formic acid, acetic acid, citric acid, oxalic acid, fluoroacetic acid, salicylic acid, fumaric acid, propionic acid, butanoic acid, 2,5-dihydroxybenzoic acid, glycolic acid, hydrochloric acid, and acetonitrile. Use of trifluoroacetic acid 0.05-5% in a saturated solution of phthalic acid (e.g., pH of about 1.5 to 3) is useful for providing solution conditions providing a high degree of specificity in the interaction of phosphorylated proteins and peptides and mesoporous metal oxide materials. In an embodiment, the contacting step is carried out at an ionic strength selected over the range of 0.01 M to 0.05 M. In an embodiment, the contacting step is carried out at a temperature selected over the range of 4 degrees Celsius to 80 degrees Celsius. For example, in some embodiments the contacting step is performed at room temperature. Solution phase components that are useful in the contacting step include, but are not limited to, phthalic acid (saturated), trifluoroacetic acid (TFA) (0.05-5%), formic acid (0.05-5%), acetic acid (0.05-5%), hydrochloric acid (3-33 mM), citric acid (0.5-1.5 M), oxalic acid (0.1-20 mM), salicylic acid (0.001-1M), fumaric acid (0.01-1 M), propionic acid (0.1-20%), butanoic acid, 2,5-dihydroxybenzoic acid (5-50 mM), glycolic acid (0.05-2 M), acetonitrile (0-80%), and acetone (0-80%). In an embodiment, the contacting step is carried out in a binding solution comprising a saturated phthalic acid solution in 0.1% TFA in water.

The step of separating the phosphorylated compounds bound to the enrichment material from at least a portion of the sample in some embodiments comprises isolating phosphorylated compounds bound to the enrichment material from at least a portion of the sample solution that is unbound to the enrichment material. Isolation of the phosphorylated compounds bound to the enrichment material can be achieved in a number of ways. In an embodiment, for example, the bound phosphorylated compounds are isolated by removing or otherwise extracting unbound portions of the sample, for example by flowing unbound sample away from the enrichment material and/or eluting off the sample not bound to the enrichment material. In an embodiment, the separating step optionally includes centrifuging or vortexing the sample and removing (e.g., pipetting or pouring off) the supernatant component of the sample. In an embodiment, the separating step includes flowing the sample on, through or within the metal oxide mesoporous material, for example in a column chromatography format. In an embodiment, the separating step comprises removing or otherwise recovering the enrichment material having bound phosphorylated compounds from unbound portions of the sample.

For enrichment of phosphorylated compounds in complex mixtures, the separating step may be carried out under solution conditions favorable for removing unbound portions of the sample, including non-phosphorylated peptides or proteins, from the enrichment material while maintaining selective binding between the phosphorylated compounds and the enrichment material. In an embodiment, for example, the separating step is carried out under acidic conditions. In an embodiment useful for enriching phosphorylated proteins and/or peptides, for example, the separating step is carried out at a pH selected from the range of 5 to 11, and optionally at a pH selected from the range of 8 to 9. In an embodiment, the separating step is carried out at a pH equal to approximately 8.8. In an embodiment useful for enriching phosphorylated proteins and/or peptides, for example, the separating step further comprises the addition of one or more additives to the sample to maintain selective binding of phosphorylated compounds with the enrichment material and/or minimize non-selective interactions involving non-phosphorylated compounds. Useful additives for the separating step include, but are not limited to, acetonitrile (0-75%), acetone (0-75%), ammonium bicarbonate (50-200 mM), boric acid (50-200 mM), tris(hydroxymethyl)aminomethane (50-200 mM), Tri-ethanolamine (1-25%), and 4-(2-hydroxyethyl)-1-piperazineethanesulfonic acid (50 mM-200 mM). In an embodiment, the separating step is carried out at an ionic strength selected from the range of 0.02 M to 0.06 M. In an embodiment, the separating step is carried out at a temperature selected from the range of 4 degrees Celsius to 80 degrees Celsius. In some embodiments, the separating step is performed at room temperature.

The separating step may optionally include additional processing steps. In an embodiment, for example, the separating step further comprises washing the enrichment material having the bound phosphorylated peptides or proteins. Washing is useful for removing non-phosphorylated compounds from the nanopores of the enrichment material. Washing may be carried out by contacting the enrichment material having bound phosphorylated compounds with one or more buffer solutions. In an embodiment, for example, a buffer is used for washing that is capable of maintaining the enrichment material in an acidic solution environment. In an embodiment, a buffer is used that maintains the pH selected over the range of 1.5-11 during the separation step. In some embodiments, for example, the washing buffer comprises an aqueous solution containing ammonium bicarbonate in water and acetonitrile (50/50).

Releasing bound phosphorylated compounds from the enrichment materials can be achieved in the present invention using a variety of techniques, including chemical reaction, physical processes and/or a change in temperature. In an embodiment, for example, the releasing step is carried out under basic conditions. In some methods, for example, the releasing step is achieved by providing a change in the solution conditions within, at the surface of and/or proximate to the enrichment materials capable of disrupting associative interactions between the enrichment material and the phosphorylated compounds. Disruption can be achieved, for example, by changing the pH or ionic strength of the solution. Alternatively, release can be achieved and/or facilitated by the addition of one or more additives to the solution, for example by addition of a releasing agent that binds to the enrichment material more strongly than the phosphorylated compound(s). Examples include, but are not limited to, the addition of ammonium hydroxide, tris(hydroxymethyl)aminomethane, acetonitrile, and/or acetone to facilitate release.

The releasing step is preferably carried out under solution conditions favorable for separating phosphorylated compounds from the enrichment material, and preferably under conditions that do not change the composition of the released phosphorylated compounds. In an embodiment, release of phosphorylated proteins and peptides is achieved under basic solution conditions, for example under a pH selected over the range of 10 to 13, and optionally under a pH selected over the range of 11 to 12. Establishing basic solution conditions can be achieved in the present invention via addition of one or more bases, such as ammonium oxide. In an embodiment, release is carried out by increasing the pH in the solution from an original value selected from the range of 1.5 to 10 to a subsequent value selected from the range of 10 to 13. In an embodiment useful for enrichment of phosphorylated proteins and peptides, release is achieved and/or facilitated by providing one or more additives to the solution containing the enrichment materials including ammonium hydroxide (25-100%), piperidine (0.5%-5%), tris(hydroxymethyl)aminomethane (50 mM-200 mM), acetonitrile (0-50%), and acetone (0-50%). In an embodiment, the releasing step is carried out at an ionic strength selected from the range of 0 M to 0.05 M. In an embodiment, the releasing step is carried out at a temperature selected over the range of 4 degrees Celsius to 80 degrees Celsius.

Release of the phosphorylated compounds may further include one or more additional processing steps. In an embodiment for example, the releasing step further comprises a step of eluting, collecting and/or removing phosphorylated compounds released from the enrichment material. In an embodiment, for example, the step of releasing the phosphorylated peptides or proteins bound to the enrichment material from the enrichment material comprises washing and/or eluting the enrichment material with one or more buffers or release agents, such as ammonium hydroxide, and/or piperidine.

Methods of the invention may optionally further comprise the step of regenerating or otherwise restore the enrichment material in a manner such that the enrichment material may be used again (or repeatedly) in a purification or enrichment process. In an embodiment, for example, the enrichment material is exposed to a pH greater than or equal to 11 for a preselected time so as to provide regeneration of the enrichment material. In an embodiment, for example, the enrichment material is exposed to a pH selected over the range of 11 to 14 for a preselected time so as to provide regeneration of the enrichment material. In some embodiments, regeneration removes compounds bound to the active surfaces of the enrichment material. In some embodiments, regeneration restores the capability of the enrichment materials to efficiently and selectively bind to phosphorylated compounds, such as phosphorylated proteins and/or peptides. In an embodiment, the enrichment material is exposed to ACN, NaOH or $NH_4OH$ after a first purification process to regenerate the enrichment material for additional purification/separation processing. In an embodiment, for example, a method of the invention further comprises the step of regenerating the enrichment material after the step of releasing the phosphorylated compounds bound to the metal oxide mesoporous material, wherein regeneration is achieved by exposing the enrichment material to a pH greater than or equal to 11.

Methods of the present invention may optionally further comprise the step of pre-treating the enrichment material(s) prior to the step of contacting the sample with the enrichment material. In an embodiment, the enrichment materials are calcined (heated to 400 degrees Celsius in air) prior to the contacting step to eliminate water and organics. In an embodiment, pre-treating the enrichment material comprises adding a binding solution to the enrichment material, such as a saturated phthalic acid solution in 0.1% TFA in water (e.g., pH over the range of 2 to 4).

The present methods are useful for enriching, purifying and otherwise isolating a range of phosphorylated compounds, particularly biomolecules including phosphorylated proteins and phosphorylated peptides. In an embodiment, the sample is a solution, such as an aqueous solution, containing the phosphorylated proteins and/or peptides. In an embodiment, the sample is a biological sample, for example a sample derived from cells or tissues, such as a serum, plasma and/or blood sample. The present methods are particularly useful for enriching phosphorylated proteins and peptides from solutions derived from a cell extract or lysate. In an embodiment, for example, the sample enriched by the present methods is predigested prior to contact with the enrichment material, for example by trypsin digestion.

In an embodiment, the method of this aspect comprises purifying and/or isolating the phosphorylated compounds, for example a method of purifying and/or isolating phosphorylated peptides and/or phosphorylated proteins in a biological sample. In an aspect, the sample containing phosphorylated peptides or proteins further comprises non-phosphorylated peptides or proteins. In another aspect, the sample containing phosphorylated peptides or proteins further comprises non-phosphorylated peptides or proteins in greater abundance than the phosphorylated peptides or proteins. In another embodiment, the sample containing phosphorylated peptides or proteins further comprises non-phosphorylated proteins or peptides, and/or other molecules.

In an aspect, the enrichment material is provided in a manner useful for practical separation applications, for example integrated in a chromatography or electrophoresis system. In an embodiment, for example, the enrichment material comprises a metal oxide mesoporous material providing an affinity material for high performance liquid chromatography, capillary electrophoresis, column chromatography, and pipette-based systems. In an embodiment, for example, the enrichment material of the present methods is provided as a monolithic column, minicolumn, filter disk, or pipet tip-based chromatographic system.

In another embodiment, the method of enriching phosphorylated peptides or proteins further comprises the step of analyzing the sample enriched in phosphorylated peptides or proteins. In an embodiment, the sample enriched in phosphorylated peptides or proteins is subsequently analyzed using a mass spectrometry (MS) technique, such as electrospray ionization (ESI) or matrix-assisted laser desorption/ionization (MALDI) mass spectrometry. In an embodiment, the sample enriched in phosphorylated peptides or proteins is subsequently analyzed using tandem mass spectrometry (MS/MS) such as collisionally activated dissociation (CAD) also known as collisionally induced dissociated (CID), electron capture dissociation (ECD), electron transfer dissociation (ETD), infrared multiphoton dissociation (IRMPD), or blackbody infrared radiative dissociation (BIRD).

In another aspect, the present invention provides a kit for enrichment of phosphorylated compounds, such as phosphorylated proteins or peptides, provided in a sample. In an embodiment, a kit comprises: (i) an enrichment material comprising a metal oxide mesoporous material(s); and (ii) instructions enabling use of the kit for the methods of the present invention for enriching phosphorylated compounds, such as phosphorylated proteins or peptides, in a sample. Instructions provided with the enrichment material in kits of the present invention may provide a description of any of the methods described herein, particularly methods including contacting, separating, releasing, pretreating and/or analyzing steps. Enrichment materials useful in this aspect include the metal oxide mesoporous materials described throughout this application, including transition metal oxide mesoporous materials and Group IIIA metal oxides mesoporous materials.

In another aspect, the present invention provides a method for enriching phosphorylated peptides or proteins in a solution comprising the steps of: (i) providing the solution containing the phosphorylated peptides or proteins; (ii) contacting the solution with an enrichment material comprising a metal oxide mesoporous material(s); wherein at least a portion of the phosphorylated peptides or proteins selectively binds to the metal oxide mesoporous material, the metal oxide selected from the group consisting of $ZrO_2$, $HfO_2$, $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, and the mixed oxides between them, such as $Zr_xHf_{1-x}O_2$ (wherein $0<x<1$), $Zr_xTi_{1-x}O_2$ (wherein $0<x<1$), $Ti_xHf_{1-x}O_2$ (wherein $0<x<1$), and $(Fe_{1-x}Ga_x)_2O_3$ (wherein $0<x<1$); (iii) separating the phosphorylated peptides or proteins bound to the metal oxide mesoporous material(s) from at least a portion of the solution; and (iv) releasing the phosphorylated peptides or proteins bound to the metal oxide mesoporous material(s) from the metal oxide mesoporous material(s), thereby enriching the phosphorylated peptides or proteins in the solution. In an embodiment, at least a portion of the phosphorylated compounds directly binds to the metal oxide mesoporous enrichment material.

In another aspect, the present invention provides a method of analyzing phosphorylated proteins in a sample; the method comprising: (i) digesting the sample containing the phosphorylated proteins; thereby generating a solution containing phosphorylated peptides; (ii) contacting the solution containing the phosphorylated peptides with an enrichment material comprising a metal oxide mesoporous material(s); wherein at least a portion of the phosphorylated peptides selectively binds to the metal oxide mesoporous material, the metal oxide selected from the group consisting of $ZrO_2$, $HfO_2$, $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, and the mixed oxides between them, such as $Zr_xHf_{1-x}O_2$ (wherein $0<x<1$), $Zr_xTi_{1-x}O_2$ (wherein $0<x<1$), $Ti_xHf_{1-x}O_2$ (wherein $0<x<1$), and $(Fe_{1-x}Ga_x)_2O_3$ (wherein $0<x<1$); (iii) separating the phosphorylated peptides bound to the metal oxide mesoporous material(s) from at least a portion of the solution containing the phosphorylated peptides; (iv) releasing the phosphorylated peptides bound to the metal oxide mesoporous material(s) from the metal oxide mesoporous material(s), thereby generating a sample enriched in the phosphorylated peptides; and (v) analyzing the phosphorylated peptides using a mass spectrometry technique; thereby analyzing the sample enriched in the phosphorylated peptides. In an embodiment, at least a portion of the phosphorylated compounds directly binds to the metal oxide mesoporous enrichment material.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION OF THE INVENTION

Figure 1:
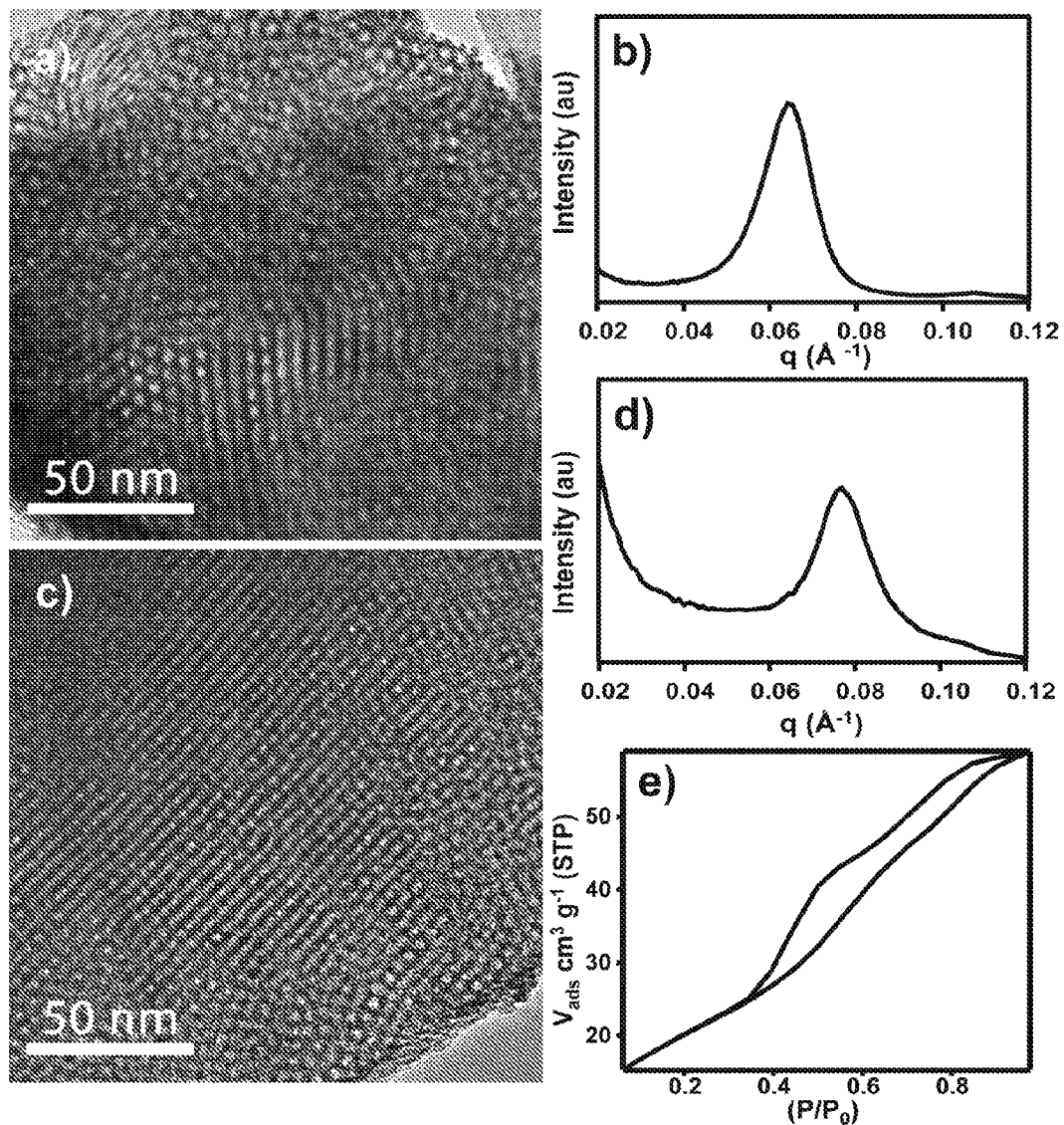
FIG. 1. Transmission electron microscope (TEM) micrograph for mesoporous $HfO_2$ (a) with its corresponding small angle X-ray scattering (SAXS) diffraction pattern (b). TEM micrograph for mesoporous $ZrO_2$ (c) with its corresponding SAXS pattern (d) and nitrogen adsorption-desorption isotherms (e).

In general, the terms and phrases used herein have their art-recognized meaning which can be found by reference to standard texts, journal references and contexts known to those skilled in the art. Referring to the drawings, like numerals indicate like elements and the same number appearing in more than one drawing refers to the same element. In addition, hereinafter, the following definitions apply and are provided to clarify their specific use in the context of the invention:

The term "metal oxide" refers broadly to compositions comprising a metal atom or combination of metal atoms bonded to one or more oxygen atoms. In some embodiments, metal oxides useful in the present invention include transition metal oxides, Group I metal oxides (Alkali metal oxides), Group II metal oxides (Alkaline earth metal oxides), Group IIIA (Also referred to as Group 13 metal (IUPAC), and including Al, Ga, In and Tl) metal oxides, lanthanide oxides, and mixtures of these. In some embodiments, metal oxides useful in the present invention also include mixed metal oxides comprising at least two different metal atoms bonded to oxygen atoms, such as at least two different metals selected from the group consisting of a transition metal, a Group I metal (Alkali metals), a Group II metal (Alkaline earth metals), a Group IIIA metal, and a lanthanide metal. Metal oxides useful in the present invention include, but are not limited to, ZrO$_2$, HfO$_2$, TiO$_2$, Ga$_2$O$_3$, Cr$_2$O$_3$, Fe$_2$O$_3$, Fe$_3$O$_4$, Al$_2$O$_3$, La$_2$O$_3$, CeO$_2$, SnO$_2$, Ta$_2$O$_5$, and the mixed oxides between them, such as Zr$_x$Hf$_{1-x}$O$_2$ (wherein 0<x<1), Zr$_x$Ti$_{1-x}$O$_2$ (wherein 0<x<1), Ti$_x$Hf$_{1-x}$O$_2$ (wherein 0<x<1), and (Fe$_{1-x}$Ga$_x$)$_2$O$_3$ (wherein 0<x<1).

The term "metal oxide mesoporous material" refers to porous metal oxide materials characterized by a plurality of pores with cross sectional dimensions (e.g., diameter or width) selected over the range of 2 to 50 nm, optionally provided in a well ordered network. Metal oxide mesoporous materials useful in the present invention may be substantially pure and comprise substantially the same metal oxide (e.g., 95% pure or optionally 99% pure). Alternatively, metal oxide mesoporous materials useful in the present invention may comprise a mixture of a plurality of different metal oxides. Metal oxide mesoporous materials may be provided as particles, and are optionally loaded together and packed to provide a column (e.g., minicolumn) or other chromatographic product (e.g., pipet tip-based product). In some embodiments, the mesoporous metal oxide is provided as a monolithic structure, and optionally as a monolithic column. In some embodiments, the mesoporous metal oxide is provided as a fiber, and optionally provided as a filter, such as a woven filter disk. Optionally, the mesoporous materials are fixed, sealed, or packaged into columns, tips, and filter disks, through monolithic synthesis, packing from particles, or weaving from fibers.

The terms "peptide" and "polypeptide" are used synonymously in the present disclosure, and refer to a class of compounds composed of amino acid residues chemically bonded together by amide bonds (or peptide bonds). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolyic digestion. Peptides and polypeptides may be generated by substantially complete digestion or by partial digestion of proteins. Identifying or sequencing a peptide refers to determination of its composition, particularly its amino acid sequence, and characterization of any modifications of one or more amino acids comprising the peptide or polypeptide.

"Protein" refers to a class of compounds comprising one or more polypeptide chains and/or modified polypeptide chains. Proteins may be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins may also include non-naturally occurring derivatives, analogues and functional mimetics generated by chemical synthesis. Exemplary derivatives include chemical modifications such as alkylation, acylation, carbamylation, iodination or any modification that derivatizes the protein. In the present invention, proteins may be modified by labeling methods, such as metabolic labeling, enzymatic labeling or by chemical reactions. Proteins may be modified by the introduction of stable isotope tags, for example as is typically done in a stable isotope dilution experiment. Proteins of the present invention may be derived from sources, which include but are not limited to cells, cell or tissue lysates, cell culture medium obtained after cell growth, whole organisms or organism lysates, or any excreted fluid or solid from a cell or organism.

"Phosphorylation" refers to the addition of a phosphate group to a compound, such as a protein, peptide, or other molecule. "Phosphorylation site" refers to the location of a phosphate group in a compound. In some contexts, phosphorylation can refer to a labile post-translational modification of a protein or a reversible post-translational modification of a protein. A "phosphorylated compound" refers to a compound, such as a protein or peptide, that has undergone phosphorylation. Phosphorylated compounds may have one or more phosphate groups, and/or derivatives thereof, wherein the phosphate groups may be in a neutral state or negatively charged state (e.g., $-1$, $-2$, or $-3$ anionic states) depending on solution conditions, such as pH. "Phosphoprotein" and "phosphopeptide" refer to phosphorylated proteins and phosphorylated peptides, respectively. In an embodiment, singularly, doubley, triply, quadruply, quintuply, or etc. phosphorylated peptides or proteins refer to peptides or proteins having one, two, three, four, five, or etc. phosphorylation sites, respectively.

"Monolithic structure" refers to a structure having one or more components within a single continuous or unitary body, and includes structures having a uniform or non-uniform composition. In some embodiments of the present invention, for example, a metal oxide mesoporous material comprises a unitary structure.

"Organofunctionalized" refers to the addition of an organic functional group. In an embodiment of the present invention, organofunctionalized is used to refer to metal oxide mesoporous materials having exposed surfaces that are not organofunctionalized, and therefore lacking an organic functional group.

Proteomics is becoming an indispensable research tool with the potential to broadly impact biological research and laboratory medicine. However, the unique characteristics of the proteome including high dynamic range in protein abundance, extreme complexity, and heterogeneity due to the various post-translational modifications, present tremendous challenges. The present invention provides methods and devices combining advances in mass spectrometry and nanotechnology, particularly for characterizing proteins with complex post-translational modifications as well as protein-protein and protein-small molecule interactions. Post-translational modifications, which usually occur in low abundance, are of critical importance for understanding the biological functions of proteins. We disclose nanoscale or nanostructured materials to enrich the low abundant proteins or peptides, which allow for more effective applications of mass spectrometric techniques for investigating important post-translational modifications, such as phosphorylation and glycosylation, and protein-protein or protein-small molecule interactions. Additionally, we disclose a method for enrichment of phosphopeptides using mesoporous nanomaterials, and results acquired using mass spectrometry confirm significant enrichment of phosphorylated peptide digests of standard purified proteins.

Phosphorylations are extremely important in signal transduction between cells and regulation of cell processes in eukaryotic organisms. However, phosphorylated proteins only occur in low stoichiometric ratios compared to non-phosphorylated proteins, hence, enrichment of phosphopeptides is essential for bottom-up or top-down identification of phosphorylation sites. Certain metal oxides, such as $ZrO_2$, $HfO_2$, $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, and the mixed oxides between them, such as $Zr_xHf_{1-x}O_2$ (wherein $0<x<1$), $Zr_xTi_{1-x}O_2$ (wherein $0<x<1$), $Ti_xHf_{1-x}O_2$ (wherein $0<x<1$), $(Fe_{1-x}Ga_x)_2O_3$ (wherein $0<x<1$) have proper amphetoric surface properties for preferable and reversible binding to the phosphate groups on phosphorylated peptides and proteins. Mesoporous zirconium and hafnium oxides (mesoporous materials have nanometer scale through pores of about 5-20 nm) have very large surface areas (several hundred $m^2$ per gram), flow through capacity, are chemically stable and robust, and can be easily prepared. They provide a low cost, effective method for enrichment of phosphorylated peptides. In an embodiment, we use commercially available amphiphilic block copolymers as surfactants to form ordered nanoscale micellular structures in suitable solutions to template the controlled hydrolysis of corresponding metal salts to produce mesoporous nanostructured metal oxides. The solvent is then removed and samples are calcined at high temperature to acquire dry and organics-free materials. Although many samples of such mesoporous oxides have been produced for $ZrO_2$ and $HfO_2$, other oxides, such as $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, and the mixed oxides between them, such as $Zr_xHf_{1-x}O_2$, (wherein 0<x<1), $Zr_xTi_{1-x}O_2$ (wherein 0<x<1), $Ti_xHf_{1-x}O_2$ (wherein 0<x<1), and $(Fe_{1-x}Ga_x)_2O_3$ (wherein 0<x<1), are possible to prepare as well.

In an embodiment, the enrichment procedure using these nanostructured oxides is as follows: load the digested proteins into a centrifuge tube with pretreated mesoporous zirconium or hafnium oxide powder; and elute the phosphopeptide with the proper buffer. The enriched samples are analyzed with mass spectrometry to evaluate the enrichment. Significant enrichment is achieved with $ZrO_2$ and $HfO_2$ of singly, doubly, and triply phosphorylated peptides, although enrichment with other oxides, such as: $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, and the mixed oxides between them, such as $Zr_xHf_{1-x}O_2$ (wherein 0<x<1), $Zr_xTi_{1-x}O_2$ (wherein 0<x<1), $Ti_xHf_{1-x}O_2$ (wherein 0<x<1), and $(Fe_{1-x}Ga_x)_2O_3$ (wherein 0<x<1) is within the scope of the invention. The enriched phosphopeptides are further analyzed using high resolution tandem mass spectrometry (MS/MS) such as electron capture dissociation (ECD) and electron capture dissociation (ETD), which are effective techniques for characterizing labile post-translational modifications such as phosphorylation.

In other embodiments of the present invention, these mesoporous materials are loaded and packed into minicolumns or pipet tip-based chromatographic products. Additionally, these mesoporous nanostructured materials are prepared in situ as "monolithic" columns. Additionally, the mesoporous metal oxide materials can be prepared as fiber forms and further woven into filters and other forms to be used in various packaged devices.

The invention may be further understood by the following non-limiting examples.

EXAMPLE 1

Mesoporous Metal Oxide Nanomaterials Effectively Enrich Phosphopeptides for Mass Spectrometry-based Phosphoproteomics Reversible protein phosphorylation is a ubiquitous post-translational modification that plays a vital role in the control of many biological processes such as cellular growth, division, and signaling.[1] Aberrant phosphorylation is known to be one of the underlying mechanisms for many human diseases, most notably cancer[1a,c]

Mass spectrometry (MS) has emerged as the most important and powerful tool for the analysis of protein phosphorylation due to its sensitivity, speed, simplicity, separation, and specificity.[2] While MS techniques have been successfully applied to determine the phosphorylation state of single proteins/peptides, MS analysis of phosphorylation on a proteome-wide scale still poses substantial challenges due to the low abundance of phosphoproteins and substoichiometric phosphorylation.[3] Therefore, isolation and enrichment of the phosphoproteins/peptides are essential for MS-based phosphoproteomics. Whereas a plethora of techniques have been developed for enriching phosphopeptides,[4] the affinity based method, immobilized metal ion affinity chromatography (IMAC)[5] using Ga(III), Fe(III), or other metals, is most widely used for phosphopeptides enrichment. Recently microparticles of titanium dioxide (TiO2),[6a,b] zirconium oxide (ZrO2),[6c] and other metal oxides[6d-e] have demonstrated higher specificity for trapping phosphate than the conventional IMAC beads since such oxides rely on specific and reversible chemisorption of phosphate groups on their amphoteric surface and have less non-specific binding. Additionally, nanoparticles, such as $ZrO_2$, $TiO_2$, $Fe_2O_3$, and titania-coated magnetic iron oxide ($Fe_3O_4@TiO_2$) nanoparticles, have recently been explored due to their potential higher capacities than the microparticles.[7]

Mesoporous materials are nanostructured materials with pore sizes typically between 2-50 nm.[8] They have extremely large surface areas and have been utilized in many applications such as catalyst support and filtration. Such large surface areas, together with the many active surface sites, can translate into even higher loading capacity for binding phosphate groups than micro- and nanoparticles. In addition to their well-ordered nanoscale porous structures and flow-through capacity, they are chemically stable and can be easily prepared at reasonable cost. All these attributes would make them ideal for applications in MS-based phosphoroproteomics. In this Example, we describe the utility of mesoporous hafnium dioxide ($HfO_2$) and $ZrO_2$ nanomaterials for simple and efficient enrichment of phosphopeptides with high specificity.

We chose the $HfO_2$ and $ZrO_2$ metal oxides because of their amphoteric surface properties,[9] which facilitates preferable and reversable binding and release of the phosphate groups under different pH of the solutions. We synthesized mesoporous materials using commercially available Pluronic® triblock copolymer surfactant F127 to form ordered nanoscale micellular structures in alcohol solutions to template the controlled hydrolysis of the metal precursors in a so-called evaporation induced self assembly (EISA) process.[8b,8c] The calcined materials were characterized with transmission electron microscopy (TEM) and small angle x-ray scattering (SAXS) to examine the quality of the mesoporous structure and determine pore size and periodicity. FIGS. 1a and 1c clearly show the ordered mesostructures of $HfO_2$ and $ZrO_2$. Average pore size was determined from TEM images to be 5.8 nm for $ZrO_2$ and 7.3 nm for $HfO_2$. Average periodicity was determined by both SAXS and TEM to be 8.2 nm for $ZrO_2$ and 10.1 nm for $HfO_2$. Brunauer-Emmett-Teller (BET) analysis of $N_2$ absorption experiments revealed that the mesoporous $ZrO_2$ has a high surface areas of 72 $m^2/g$, which is in good agreement with that previously reported for meosporous $ZrO_2$ templated with this block copolymer F127.[8e] The high surface area, which can be further increased when other surfactants are used,[8] makes mesoporous materials good candidates for phosphopeptide enrichment.

Figure 2:
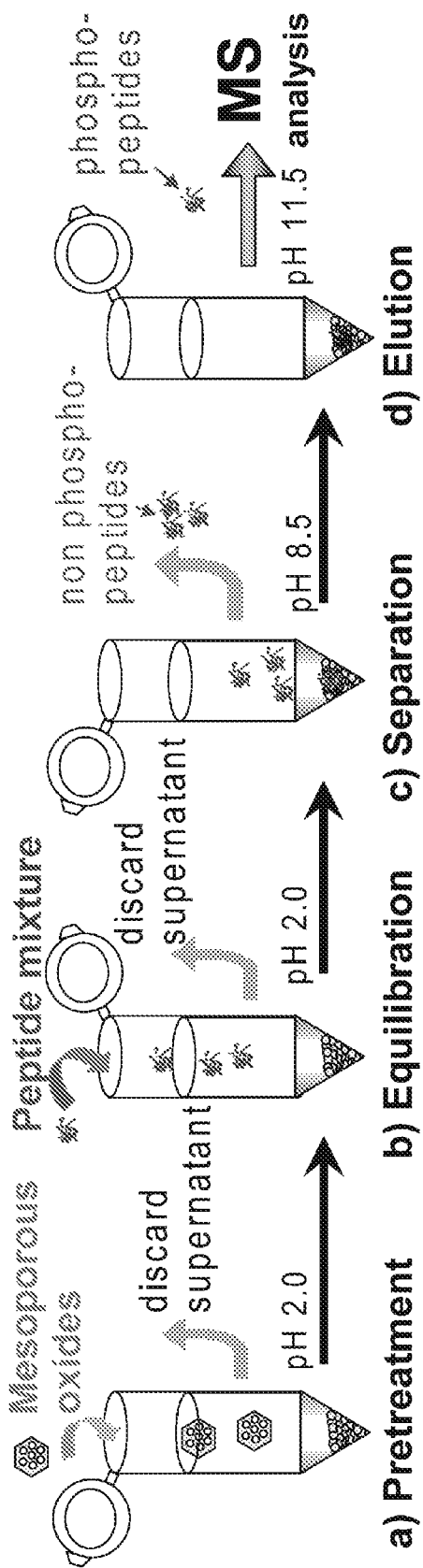
FIG. 2. Flow diagram of a phosphopeptide enrichment procedure.
Figure 3:
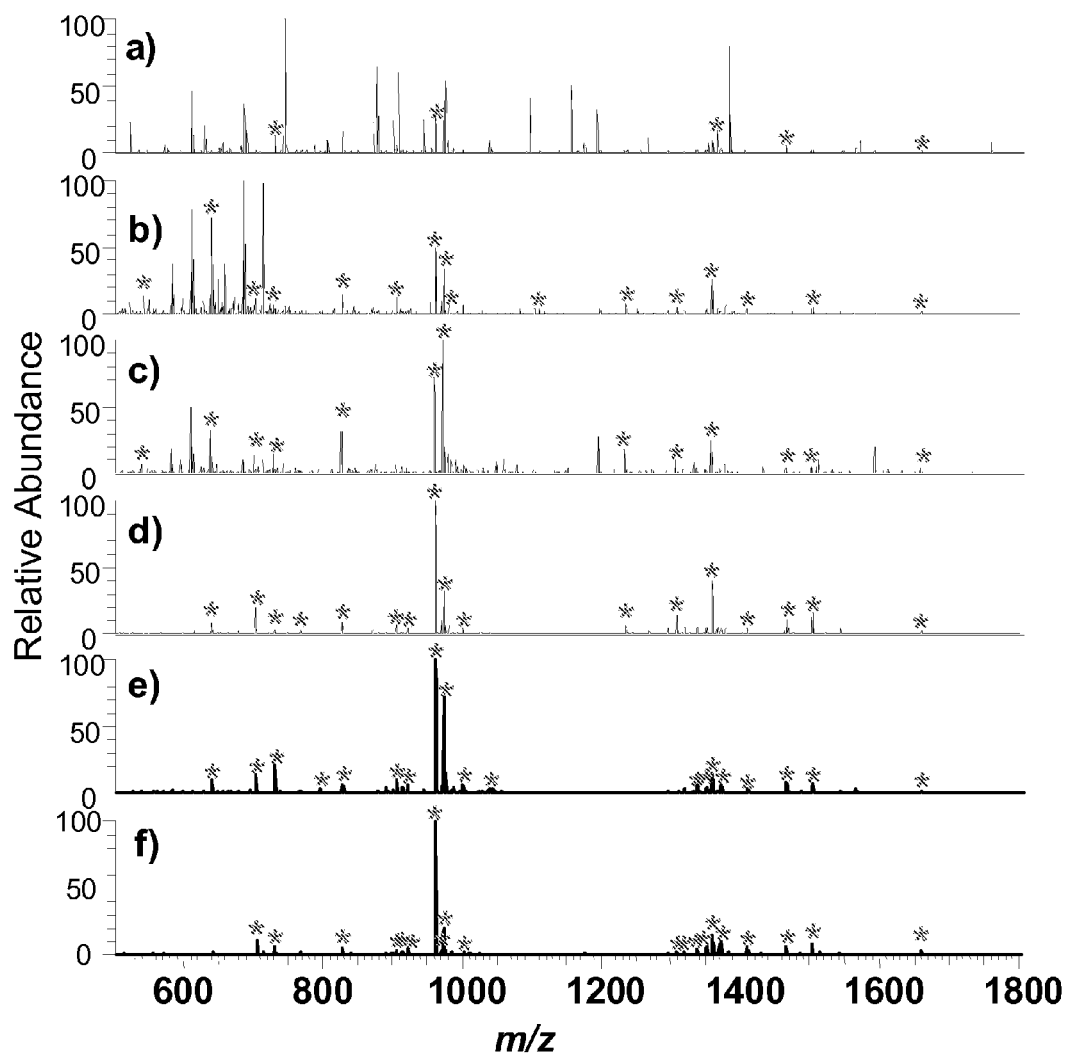
FIG. 3. Negative ion mode ESI FTMS spectra from a tryptic digest of α-casein, (a) before enrichment; (b) after $ZrO_2$ enrichment with 0.1% TFA as binding buffer, $H_2O$ as washing buffer and piperidine (pH 11.5) as the eluting buffer; (c) after $ZrO_2$ enrichment with 0.1% TFA as binding and washing buffers and piperidine (pH 11.5) as the eluting buffer; (d) after $ZrO_2$ enrichment with 0.1% TFA as binding buffer, 50 mM $NH_4HCO_3$ in $H_2O$ as the washing buffer and piperidine (pH 11.5) as the eluting buffer; (e) after $ZrO_2$ enrichment with 0.1% TFA in a saturated solution of phthalic acid as the binding buffer, 50 mM $NH_4HCO_3$ in 50/50 water/ACN as the washing buffer and $NH_4OH$ (pH 11.5) as the eluting buffer; (f) 20 mg/mL phthalic acid in 0.1% TFA 50/50 ACN/$H_2O$, wash with 50 mM $NH_4HCO_3$ in 50/50$H_2O$/ACN as the washing buffer and NH$_4$OH (pH 11.5) as the eluting buffer. Asterisks indicate identified phosphopeptides.

The enrichment procedures using mesoporous metal oxides is shown in FIG. 2 and includes: (a) pretreatment of mesoporous oxides, (b) equilibration of the peptide mixtures with mesoporous oxides at pH 2.0, (c) separation of the unbound non phosphopeptides by removing the supernatant solutions at pH 8.5, and (d) elution of the phosphopeptides at pH 11.5. Strong binding of the phosphate groups to $HfO_2$ and $ZrO_2$ surface allows the phosphorylated peptides to remain absorbed on the mesoporous materials until eluted with a high pH solution, because this specific binding is reversible under different conditions due to the amphotericity. Non-specific binding, presumably from acidic peptides, has been minimized by optimizing the buffers used in binding, washing, and eluting steps (See, FIG. 3). Good results (See, FIG. 3f) were achieved with a binding buffer solution of 20 mg/mL phthalic acid in 0.1% trifluoroacetic acid in 50/50 water/acetonitrile (pH 2.0), washing twice with 50 mM ammonium bicarbonate in 50/50 water/acetonitrile (pH 8.5), and an eluting buffer of ammonium hydroxide (pH 11.5). The eluted phosphopeptide solutions were then adjusted properly to be analyzed by electrospray (ESI) MS.

Figure 4:
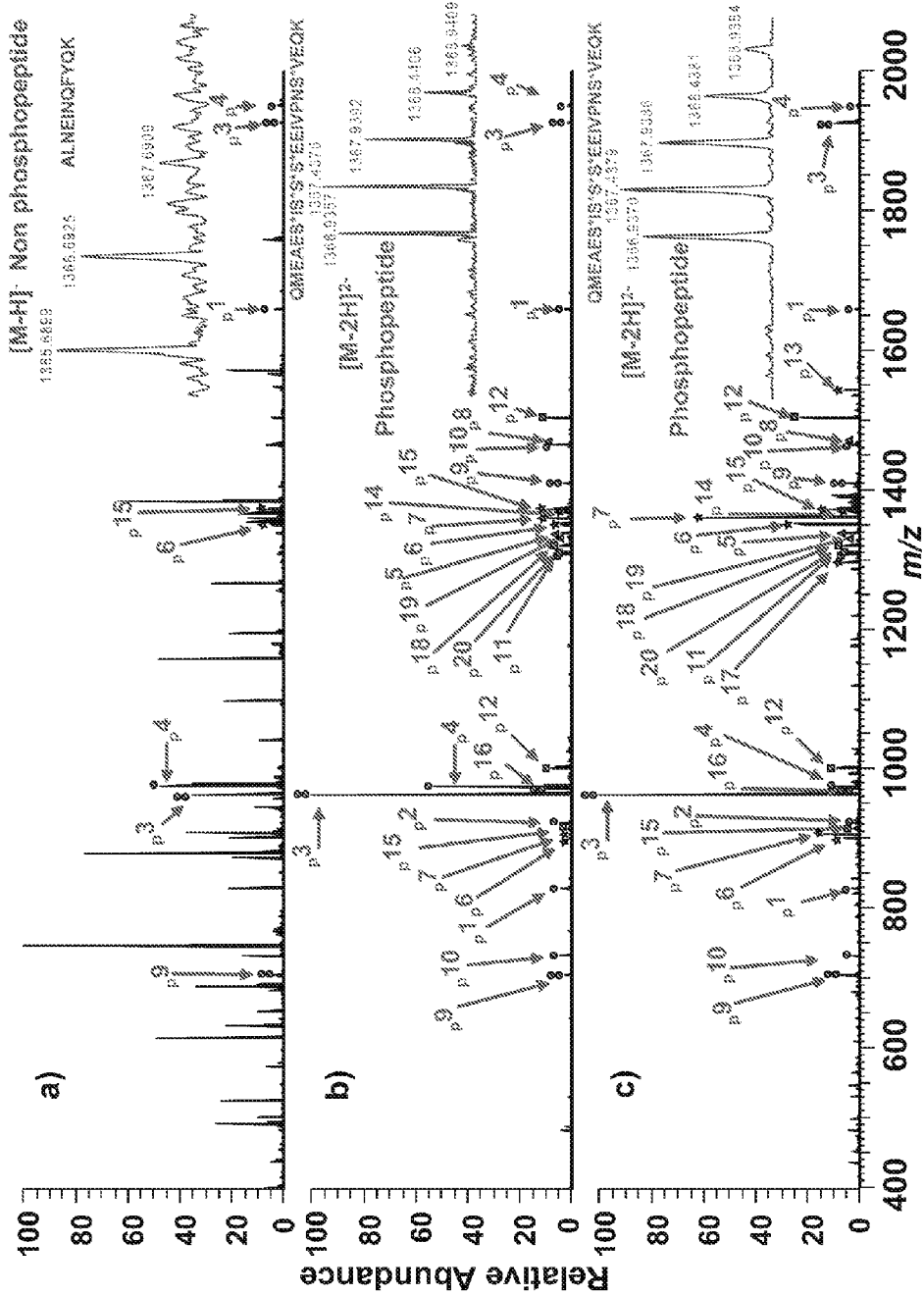
FIG. 4. Negative ion mode ESI/FTMS spectra of peptide mixtures digested from α-casein with trypsin acquired before enrichment (a), and after enrichment with mesoporous ZrO$_2$ (b) and HfO$_2$ (c). Circle, double circle, triangle, square, and star indicate singly, doubly, triply, quadruply and quintuply phosphorylated peptides, respectively. Phosphopeptides labeled with numbers are identified and shown in Table 2. Insets are expanded MS spectra at m/z 1365-1369; a singly charged non phosphopeptide at m/z 1366 in (a), and a doubly charged quintuply phosphorylated peptide, p14, at m/z 1367 in (b, c).

The enrichments using mesoporous $HfO_2$ and $ZrO_2$ are extremely effective as shown by the high resolution Fourier transform (FT) MS spectra of the α-casein digest before and after the enrichment (See, FIG. 4). Only 8 MS peaks corresponding to 6 phosphopeptides were detected before enrichment (See, FIG. 4a); all of which are low abundance peaks owing to ion suppression from abundant non phosphopeptides. In contrast, after enrichment with mesoporous $ZrO_2$ (See, FIG. 4b), 27 multiply charged MS peaks corresponding to 18 phosphopeptides were detected in a single mass spectrum with much higher signal-to-noise ratios. After enrichment with $HfO_2$ (See, FIG. 4c), 29 multiply charged MS peaks corresponding to 20 phosphopeptides were detected. Enrichment with mesoporous $HfO_2$ yields higher intensity for multiply phosphorylated peptides and revealed multi-phosphorylated peptides p17 and p13 which were not previously observed for the mixtures enriched by mesoporous $ZrO_2$. In both cases nearly all of the non phosphopeptides were removed by the enrichment procedure leaving all abundant peaks to be phosphopeptides, which substantially enhanced the signal of phosphopeptides. The insets in FIG. 4 highlight a quintuply phosphorylated peptide, p14, which was completely suppressed by non phosphopeptides without enrichment (See, FIG. 4a) and was observed only after enrichment (See, FIG. 4b, c) underscoring the effectiveness of this enrichment procedure. Such highly effective and specific enrichment of phosphopeptides out of the peptide mixtures with mesoporous $HfO_2$ and $ZrO_2$, which could be considered as "purification", allows more robust analysis of the phosphopeptides.

Figure 5:
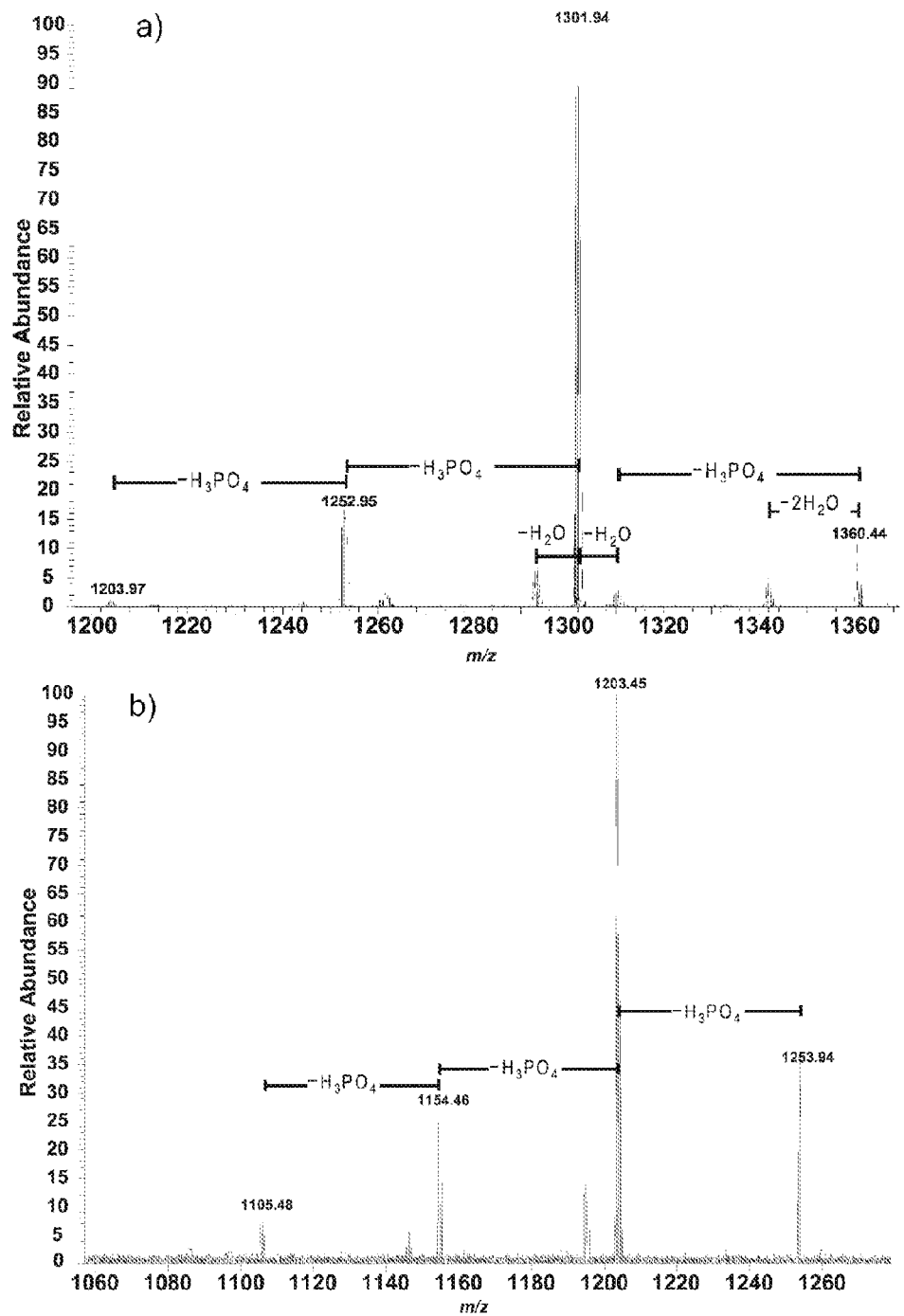
FIG. 5. Negative ion mode CAD MS/MS (a) and MS$^3$ (b) spectra of a quintuply phosphorylated peptide $_p$7, showing a loss of 5 phosphorylations. Parent peak in (A) is m/z 1360.44. For MS$^3$ m/z 1252.95 was isolated from (a) and fragmented (b).

The phosphopeptides were first detected based on the facile neutral loss of phosphoric acid ($H_3PO_4$) or metaphosphoric acid ($HPO_3$) from phosphorylated serine/threonine/tyrosine phosphopeptides generated from collisionally activated dissociation (CAD), a conventional tandem mass spectrometry (MS/MS) method (e.g. See, FIG. 5). The sequences of the enriched phosphopeptides were further confirmed and the phosphorylation sites within phosphopeptides were unambiguously localized by both CAD and electron capture dissociation (ECD) (e.g. See, FIG. 6). Fragment ions were assigned with very high mass accuracy (<5 ppm) (See, Table 1 and 2). The specificity of the enrichment enabled easy isolation of the peaks and the large trapping capacity of the mesoporous materials yielded highly abundant peaks which, upon fragmentation, gave complete or nearly complete coverage for the peptides of interest (e.g. See, FIG. 6b). Unlike CAD which tends to knock off the phosphate groups (e.g. See, FIG. 5, 6a), ECD[10] is a nonergodic MS/MS technique known to preserve the labile phosphorylation making it extremely powerful for facile location of phosphorylation sites. However, ECD requires higher signal-to-noise ratios for precursor ions thus demands efficient enrichment processes for its effective applications in phosphoproteomics.[6c] The sequences of all the identified singularly to quintuply phosphorylated peptides in FIGS. 4b, c and 7b, c are summarized in Table 3. Overall, we have identified 20 unique phosphorylation sites (out of a total of 21 potential phosphorylation sites)[11] for α-casein (s1 and s2 variants) from a single enrichment using mesoporous $HfO_2$ or $ZrO_2$.

To further evaluate the specificity for phosphopeptides, we tested the mesoporous $HfO_2$ and $ZrO_2$ using a more complicated mixture with a substantial fraction of non phosphorylated proteins. 5 non phosphoproteins and 7% (by weight of the total proteins) phosphoprotein, α-casein (See, Table 4) were mixed and digested with trypsin to create a complex peptide mixture. Before enrichment many non phosphopeptides in this mixture dominate the MS spectrum (See, FIG. 7a) so that even the most abundant phosphopeptide, p3, is severely suppressed and hardly observable. After enrichment with mesoporous $ZrO_2$ (See, FIG. 7b), 27 multiply charged MS peaks corresponding to 18 phosphorylated peptides were identified. Similarly, enrichment by mesoporous $HfO_2$ (See, FIG. 7c) resulted in 29 multiply charged MS peaks corresponding to 20 phosphorylated peptides. Note all of the phosphopetides and phosphorylation sites identified from the peptide mixture digested from pure α-casein were also recovered from this much more complex peptide mixture, underlining the specificity of this enrichment even when used with a complex mixture.

Both mesoporous $HfO_2$ and $ZrO_2$ materials show significant enrichment of phosphopeptides in complex peptide mixtures including those phosphopeptides of very low abundance (See, FIGS. 4b,c and 7b,c). While the number of phosphopeptides identified by mesoporous $HfO_2$ and $ZrO_2$ are similar ($HfO_2$ enrichment identified two more multiply phosphorylated peptides than $ZrO_2$), $HfO_2$ appears to be more effective in enriching multiply phosphorylated peptides. For example, a quintuply phosphorylated peptide, p7, is significantly more abundant after $HfO_2$ enrichment than that of $ZrO_2$ (See, FIGS. 4b,c and 7b,c) which enables further MS/MS characterization of these highly phosphorylated peptides.

Figure 8:
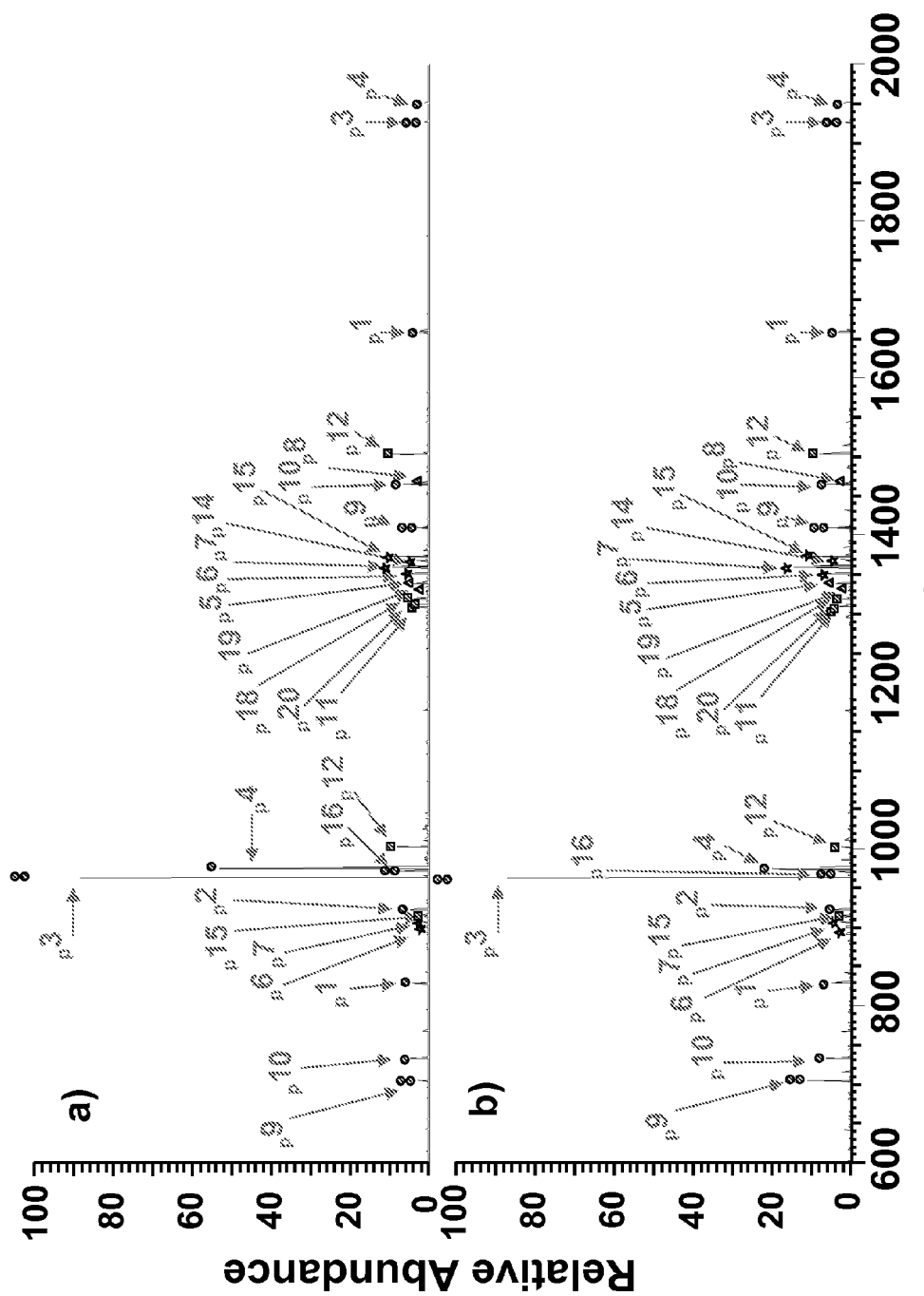
FIG. 8. Negative ion mode ESI/FTMS spectra of peptide mixtures digested from α-casein with trypsin acquired with (a) fresh ZrO$_2$ mesoporous material and (b) regenerated ZrO$_2$ mesoporous material with concentrated NaOH and ACN. Circle, double circle, triangle, square, and star indicate singly-, doubly-, triply-, quadruply- and quintuply phosphopeptides, respectively. Phosphopeptides labeled with numbers are identified and shown in Table 3.
Figure 9:
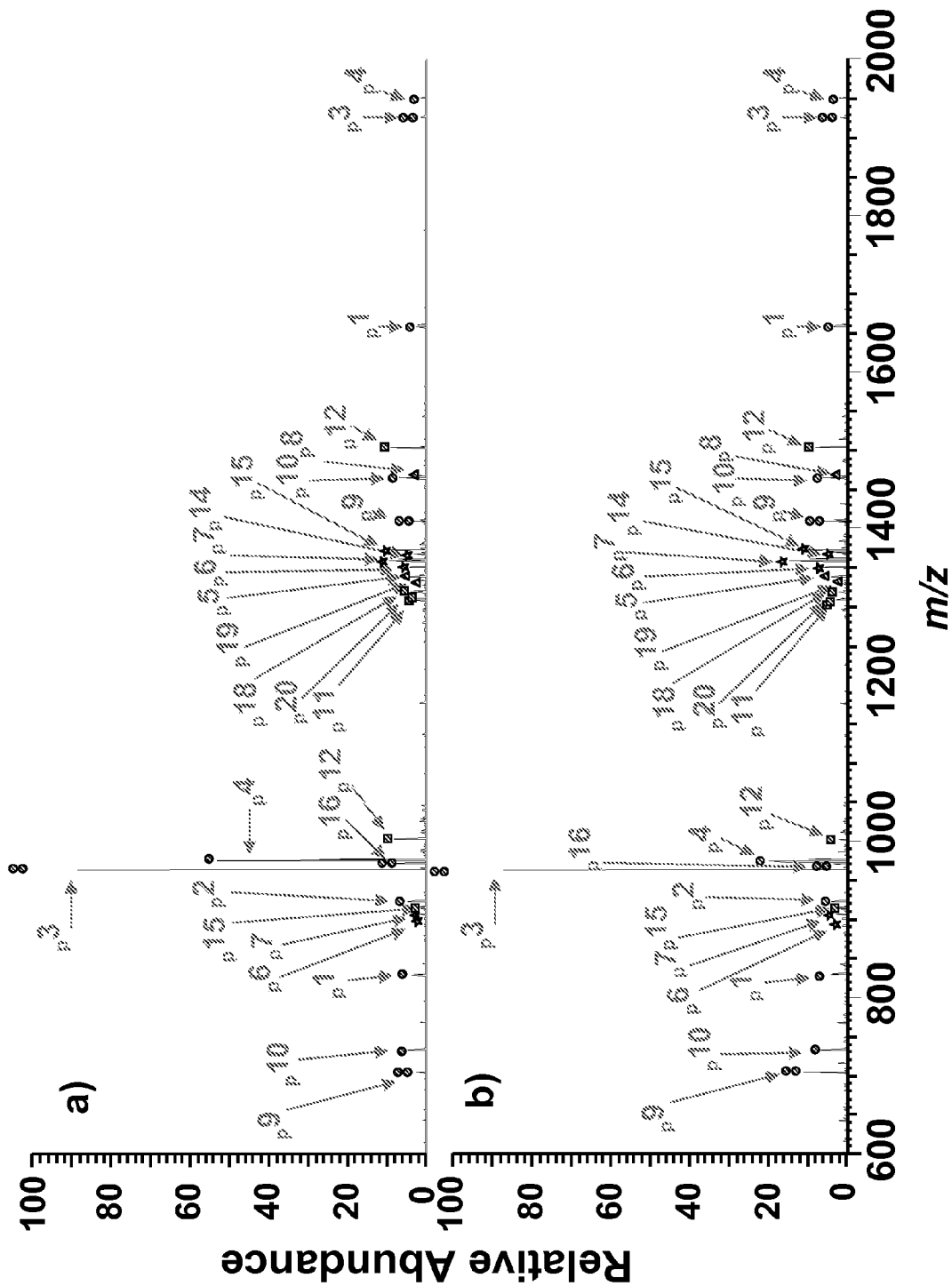
FIG. 9. Negative ion mode ESI/FTMS spectra of peptide mixtures digested from α-casein with trypsin acquired with fresh HfO$_2$ mesoporous material (a) and regenerated HfO$_2$ (b) mesoporous material with concentrated ammonium hydroxide and acetonitrile. Circle, double circle, triangle, square, and star indicate singly-, doubly-, triply-, quadruply- and quintuply phosphopeptides, respectively. Phosphopeptides labeled with numbers are identified and shown in Table 3.
Figure 10:
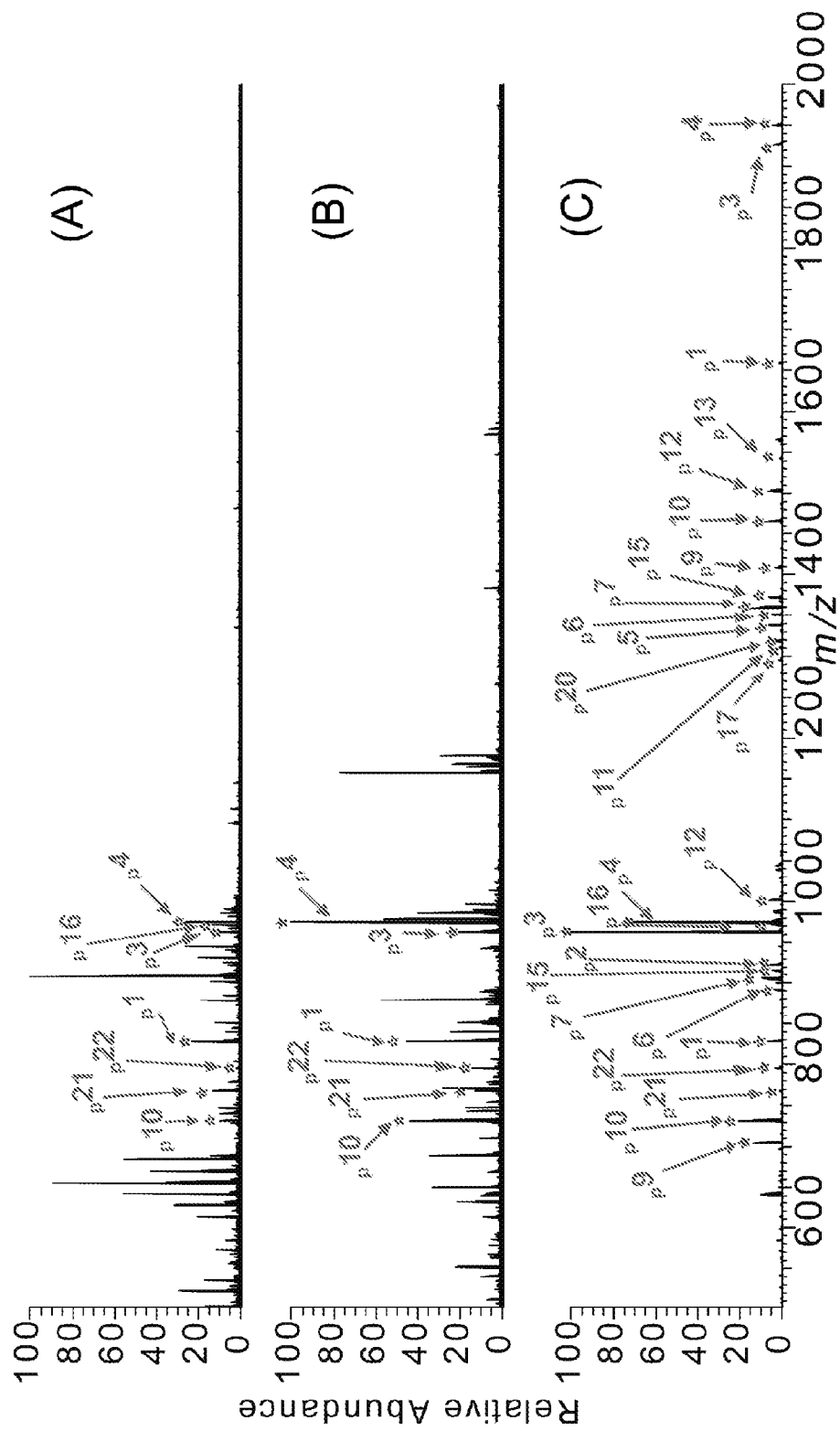
FIG. 10. Comparison of the mesoporous ZrO$_2$ nanomaterial with leading commercial products for phosphopeptide enrichment. Negative ion mode ESI/FTMS spectra of peptide mixtures digested from α-casein with trypsin acquired after enrichment with (a) a leading commercial IMAC-based product, (b) a leading commercial product of ZrO$_2$ packed tip, and (c) the mesoporous ZrO$_2$ reported herein. Phosphopeptides are labeled with numbers that are identified and shown in Table 3.

These chemically stable and robust mesoporous materials can be reused for multiple enrichments. Even after exposure to phthalic acid, mesoporous materials can be regenerated simply by soaking with acetonitrile and ammonium hydroxide. The first-versus the second-use of the same mesoporous materials appear to have similar efficacy for enriching phosphopeptides (See, FIGS. 8 & 9). Furthermore, in side-by-side comparisons of the mesoporous materials with the standard commercially available product for phosphopeptide enrichment, the mesoporous $ZrO_2$ showed significantly higher specificity for phosphopeptide enrichment over this leading product, $ZrO_2$ microtips (See, FIG. 10). After enrichment with the IMAC-based enrichment product (FIG. 10a), 7 multiply charged MS peaks corresponding to 7 phosphopeptides were identified in one MS spectrum. Enrichment with the $ZrO_2$ packed tips (FIG. 10b) revealed 6 multiply charged MS peaks corresponding to 6 phosphopeptides in one MS spectrum. In contrast, an enrichment with the mesoporous $ZrO_2$ nanomaterials detected 27 multiply-charged MS peaks corresponding to 19 phosphopeptides (FIG. 10c)

In conclusion, we demonstrate the use of mesoporous $HfO_2$ and $ZrO_2$ nanomaterials for simple and highly effective enrichment of phosphopeptides. Whereas both materials enrich phosphopeptides with high specificity, mesoporous $HfO_2$ has further advantages for enriching multiply phosphorylated peptides as well as singly phosphorylated peptides, which allows a more comprehensive and efficient phosphoproteomic analysis. Proper engineering of the mesoporous materials in terms of chemical composition, porosity, surface area, and pore structures and further optimization of the enrichment procedures will likely enhance their performance even further. These results open up the exploitation of this and other mesoporous nanomaterials for their practical applications in MS-based phosphoproteomic study of complex biological samples.

Experimental Section

Mesoporous $HfO_2$ and $ZrO_2$ were synthesized from reported previously with minor changes.[8b,8] About 100 μL of peptide mixtures digested from α-casein (effective concentration 4 pmol/μL) or a 6-protein mixture consisted of α-casein, serum albumin, ubiquitin, ribonuclease B, β-lactoglobulin from bovine, and troponin porcine skeletal muscle (see, Table 4) were loaded into a 1.5 mL centrifuge tube containing 4 mg pretreated mesoporous $ZrO_2$ or $HfO_2$ powder. After equilibration with digested peptides using a solution of 20 mg/mL phthalic acid in a solution of 0.1% TFA in 50:50 acetonitrile/water at pH 2.0, the unbound non phosphopeptides were washed off twice with 1 mL of 50 mM ammonium bicarbonate solution in 50:50 acetonitrile: water at pH 8.5. Then the phosphopeptides were eluted from the mesoporous oxides with ammonium hydroxide solution (pH 11.5). The eluted peptides were either directly used in negative ion mode MS analysis or dried down and reconstituted in a solution of 0.1-5% formic acid in 50:50 acetonitrile/water for positive ion mode MS analysis. MS data were acquired on either a standalone LTQ mass spectrometer coupled with a two-dimensional liquid chromatography (2D-LC) or a high resolution linear trap/FTICR hybrid mass spectrometer (LTQ FT Ultra, Thermo Scientific Inc).

REFERENCES

[1] a) T. Hunter, Cell 2000, 100, 113-127; b) T. Pawson, P. Nash, *Science*, 2003, 300, 445-452; c) H. Jumaa, R. W. Hendricks, M. B. Reth, *Annu. Rev. Immunol.* 2005, 23, 415-445.

[2] a) F. W. McLafferty, E. K. Fridriksson, D. M. Horn, M. A. Lewis, R. A. Zubarev, *Science* 1999, 284, 1289-1290; b) D. T. McLachlin, B. T. Chait, *Curr. Opin. Chem. Biol.* 2001, 5, 591-602; c) P. H. Huang, F. M. White, *Mol. Cell* 2008, 31, 777-781; d) E. Salih,; *Mass Spec. Rev.* 2005, 24, 828-846; e) S. A. Carr, M. J. Huddleston, R. S. Annan, *Anal. Biochem.* 1996, 239, 180-192.

[3] a) M. Mann, S. E. Ong, M. Gronborg, H. Steen, O. N. Jensen, A. Pandey, *Trends Biotechnol.* 2002, 20, 261-268; b) H. Steen, J. A. Jebanathirajah, J. Rush, N. Morrice, M. W. Kirschner, *Mol. Cell. Proteomics* 2006, 5, 172-181.

[4] a) B. Bodenmiller, L. N. Mueller, M. Mueller, B. Domon, R. Aebersold, *Nat. Methods* 2007, 4, 231-237; b) H. Zhou, J. D. Watts, R. Aebersold, *Nat. Biotechnol.* 2001, 19, 375-378; c) Y. Oda, T. Nagasu, B. T. Chait, *Nat. Biotechnol.* 2001, 19, 379-382; d) W. A. Tao, B. Wollscheid, R. O'Brien, J. K. Eng, X. J. Li, B. Bodenmiller, J. D. Watts, L. Hood, R. Aebersold, *Nat. Methods* 2005, 2, 591-598; e) M. B. Goshe, T. P. Conrads, E. A. Panisko, N. H. Angell, T. D. Veenstra, R. D. Smith, *Anal. Chem.* 2001, 73, 2578-2586.

[5] a) J. Porath, J. Carlsson, I. Olsson, G. Belfrage, *Nature* 1975, 258, 598-599; b) M. C. Posewitz, P. Tempst, *Anal. Chem.* 1999, 71, 2883-2892; c) X. Zhang, J. Y. Ye, O. N. Jensen, P. Roepstorff, *Mol. Cell. Proteomics* 2007, 6, 2032-2042; d) S. B. Ficarro, M. L. McCleland, P. T. Stukenberg, D. J. Burke, M. M. Ross, J. Shabanowitz, D. F. Hunt, F. M. White, *Nat. Biotechnol.* 2002, 20, 301-305; e) A. Wolf-Yadlin, S. Hautaniemi, D. A. Lauffenburger, F. M. White, *Proc. Natl. Acad. Sci. U.S.A.* 2007, 104, 5860-5865.

[6] a) M. W. H. Pinkse, P. M. Uitto, M. J. Hilhorst, B. Ooms, A. J. R. Heck, *Anal. Chem.* 2004, 76, 3935-3943; b) M. R. Larsen, T. E. Thingholm, O. N. Jensen, P. Roepstorff, T. J. D. Jorgensen, *Mol. Cell. Proteomics* 2005, 4, 873-886; c) H. K. Kweon, K. Hakansson, *Anal. Chem.* 2006, 78, 1743-1749; d) L. Han, Z. Shan, D. H. Chen, X. J. Yu, P. Y. Yang, B. Tu, D. Y. Zhao, *J. Colloid. Interface Sci.* 2008, 318, 315-321; e) S. B Ficarro, J. R. Parikh, N. C. Blank, J. A. Marto, *Anal. Chem.* 2008, 80, 4606-4613.

[7] a) C. T. Chen, Y. C. Chen, *Anal. Chem.* 2005, 77, 5912-5919; b) H. J. Zhou, R. J. Tian, M. L. Ye, S. Y. Xu, S. Feng, C. S. Pan, X. G. Jiang, X. Li, H. F. Zou, *Electrophoresis* 2007, 28, 2201-2215; c) G. Han, M. Ye, H. Zou, *Analyst*, 2008, 133, 1128-1138.

[8] a) P. D. Yang, D. Y. Zhao, D. I. Margolese, B. F. Chmelka, G. D. Stucky, *Nature* 1998, 396, 152-155; b) P. D Yang, D. Y. Zhao, D. I. Margolese, B. F. Chmelka, G. D. Stucky, *Chem. Mater.* 1999, 11, 2813-2826; c) C. J. Brinker, Y. F. Lu, A. Sellinger, H. Y. Fan, *Advanced Materials*. 1999, 11, 579-585; d) Y. F. Lu, R. Ganguli, C. A. Drewien, M. T. Anderson, C. J. Brinker, W. L. Gong, Y. X. Guo, H. Soyez, B. Dunn, M. H. Huang, J. I. Zink, *Nature* 1997, 389, 364-368; e) J. Fan, S. W. Boettcher, G. D. Stucky, *Chem. Mater.* 2006, 18, 6391-6396; f) B. Tian, H. Yang, X. Liu, S. Xie, C. Yu, J. Fan, B. Tu, D. Zhao *Chem. Comm.* 2002, 17, 1824-1825.

[9] a) J. Nawrocki, J. Rigney, A. McCormick, P. W. Carr, *J. Chromatogr. A* 1993, 657, 229-282; b) D. Rai, Y. X. Xia, N. J. Hess, D. M. Strachan, B. P. McGrail, *J. Solution Chem.* 2001, 30, 949-967.

[10] a) R. A. Zubarev, N. L. Kelleher, F. W. McLafferty, *J. Am. Chem. Soc.* 1998, 120, 3265-3266; b) Y. Ge, B. G. Lawhorn, M. ElNaggar, E. Strauss, J. H. Park, T. P. Begley, F. W. McLafferty, *J. Am. Chem. Soc.* 2002, 124, 672-678; c) S. D. H. Shi, M. E. Hemling, S. A. Carr, D. M. Horn, I. Lindh, F. W. McLafferty, *Anal. Chem.* 2001, 73, 19-22; d) K. Breuker, F. W. McLafferty, *Angew. Chem. Int. Ed.* 2003, 42, 4900-4904.

[11] http://www.expasy.ch/sprot/

I. Experimental Details

Materials.

Chemicals for mesoporous material synthesis. Block copolymer $HO(CH_2CH_2O)_{106}(CH_2CH(CH_3)O)_{70}(CH_2CH_2O)_{106}H$ (designated as EO106-PO70-EO106, or Pluronic F127) was provided as a gift from BASF (Florham Park, N.J.). Anhydrous precursors zirconium ethoxide (Zr$(OEt)_4$), zirconium chloride ($ZrCl_4$), hafnium chloride ($HfCl_4$) and ethanol (200 proof) were purchased from Sigma Aldrich (St. Louis, Mo.).

Materials for enrichment. α-Casein from bovine milk, bovine serum albumin (BSA), porcine troponin from skeletal muscle, bovine ubiquitin, bovine ribonuclease B, and bovine β-lactoglobulin were purchased from Sigma (St. Louis, Mo.). Trypsin was a gift from Promega (Madison, Wis.). All proteins were used as received without further purification. Ammonium bicarbonate ($NH_4HCO_3$), trifluoroacetic acid (TFA), acetic acid, acetonitrile (ACN), ammonium hydroxide ($NH_4OH$) and isopropanol were purchased from Fisher Scientific (Fair Lawn, N.J.), phthalic acid from Acros Organics (Morris Plains, N.J.) and used without further purification.

Preparation of mesoporous metal oxides. Mesoporous $ZrO_2$ was synthesized by adding Pluronic® F127 (0.5 g), $ZrCl_4$ (1.6 mmol) and Zr$(OEt)_4$ (4.3 mmol) in that order to ethanol (10 g 200 proof). The resulting solution was stirred for 2 hrs and then was transferred to petri-dishes and aged 4 days in a 40° C. incubator with humidity controlled by a saturated KCl solution. Then the as-made $ZrO_2$ was calcined at 370° C. for 2 hrs (6 hr ramp). Mesoporous $HfO_2$ was synthesized by adding Pluronic® F127 (0.1 g) and $HfCl_4$ (1 mmol) to ethanol (1 g 200 proof). To this solution 10 μL 50% $NH_4OH$ in $H_2O$ was added. The resulting solution was stirred for 2 hrs and transferred to petri-dishes and aged at 40° C. for 4 days. Then the as-made $HfO_2$ was calcined at 370° C. for 2 hrs (6 hr ramp).

Characterization of mesoporous materials. The nanostructures of the synthesized mesoporous materials were confirmed with a combination of small angle x-ray scattering (SAXS) on a Rigaku SAXS (Rigaku, Tex., USA) and transmission electron microscopy (TEM) which was taken with a Philips CM200UT (Philips Electron Optics, Eindhoven, The Netherlands) with an accelerating voltage of 200 kV. SAXS samples were prepared by grinding the samples and placing them in a u-capillary for analysis. For TEM, samples were ground and suspended in ethanol and then dispersed onto lacy carbon TEM grids for analysis. Brunauer-Emmett-Teller (BET) measurements were performed on a Quantachrome Instruments Autosorb-1 gas sorption system (Boynton Beach, Fla.) using nitrogen as the adsorbate. Samples were degassed for one hour at 213° C. prior to measurement. The nitrogen sorption curve was taken as 20 pts adsorption/20 pts desorption, with the BET surface area calculated using a 7 point BET analysis.

Proteolytic sample preparation. α-Casein was dissolved in 200 mM $NH_4HCO_3$ to a final concentration of 1 μg/μL to be used as a stock solution. Trypsin digestion was performed with an enzyme-to-protein ratio of 1:100 and incubated at 37° C. for 2 hrs. The 6-protein mixture was prepared using BSA, α-casein, troponin, ubiquitin, ribonuclease B, and β-lactoglobulin. These proteins were combined just before digestion, desalted, reduced with dithiothreitol (85 mM) for 3 hrs and then alkylated with iodoacetic acid (90 mM) for 1 hr and finally digested by trypsin (1:50) overnight. For both pure α-casein and the 6-protein mixture, the resulting digest solution was quenched with 6 μL of acetic acid, aliquoted, and stored at −20° C. The peptide solutions were diluted 10 times with 20 mg/mL phthalic acid solution in 0.1% TFA in 50/50 water/ACN (pH 2.0) just before enrichment. This brought the final concentration of α-casein before enrichment to 4 pmol/μL for the pure α-casein. The final protein concentrations and quantities of the proteins present in the 6-protein mixture before enrichment are shown in Table 4.

Procedures for enrichment of phosphopeptides using mesoporous metal oxides. In a 1.5 mL centrifuge tube, 1-4 mg of the calcined mesoporous material was weighed out and pretreated with 200 μL of a binding solution. The binding solution consisted of a 20 mg/mL phthalic acid solution in 0.1% TFA in 50/50 water/ACN (pH 2.0). The tubes were vortexed for 1 min, centrifuged for 1 min, and then the equilibrating solution was pipetted out and discarded. 100 μL of peptide solutions digested from α-casein (4 pmol/μL) or the 6-protein mixture (See, Table 4) in the binding solution were added to the mesoporous materials. The samples were mixed thoroughly for 5 mins and then centrifuged for 1 min before the supernatant was pipetted off. Then the metal oxide was rinsed twice with 1 mL of a 50 mM solution of $NH_4HCO_3$ in 50/50 water/ACN mixture (pH 8.5) following the same procedure of vortexing, spinning down, and discarding the supernatants. Finally, the phosphopeptides were eluted from the mesoporous oxide powder with an aqueous solution of ammonium hydroxide at pH 11.5 and the supernatant was collected. The eluted peptides were either directly used for negative ion mode MS analysis or dried down and reconstituted in a solution of 0.1-5% formic acid or acetic acid in 50:50 ACN/$H_2O$ for positive ion mode MS analysis.

Mass spectrometry analysis. Mass spectra were acquired on a stand alone LTQ linear ion trap mass spectrometer and a 7 T linear trap/Fourier transform ion cyclotron resonance (FTICR) hybrid mass spectrometer (LTQ FT Ultra, Thermo Scientific Inc., Bremen, Germany).

Samples were introduced to LTQ with an Eksigent nano 2D HPLC system (Eksigent Technologies, Dublin, Calif.). The phosphopeptides were detected in a neutral loss $MS^3$ acquisition mode in which the mass spectrometer was set as a full scan MS followed by data dependent MS/MS. Subsequently $MS^3$ spectrum was automatically triggered when the neutral loss of 98 Da for detection of phosphoric acid, $H_3PO_4$, (Δm/z of 98, 49, and 32.7 for 1+, 2+, 3+ charge states, respectively) and 80 Da for metaphosphoric acid ($HPO_3$) (Δm/z of 80, 40, and 26.7 for 1+, 2+, 3+ charge states, respectively). The data dependent MS/MS and $MS^3$ spectra were searched against the SwissProt non-redundant bovine and porcine protein database in Bioworks using SEQUEST algorithm considering variable phosphorylations of Ser, Thr, and Tyr residues.

The samples were introduced to the LTQ FT mass spectrometer using an automated chip-based nanoESI source, the Triversa NanoMate (Advion BioSciences, Ithaca, N.Y.) with a spray voltage of 1.2-1.6 kV versus the inlet of the mass spectrometer, resulting in a flow of 50-200 nl/min. Ion transmission into the linear trap and further to the FTICR cell was automatically optimized for maximum ion signal. The target values (the approximate number of accumulated ions) for a full MS scan linear trap (LT) scan, FTICR cell (FT) scan, $MS^n$ linear trap scan and $MS^n$ FTICR scan were $3 \times 10^4$, $10^6$, $10^4$, and $5 \times 10^5$, respectively. The resolving power of the FTICR mass analyzer was set at 100,000 m/$\Delta m_{50\%}$ at m/z 400, resulting in an acquisition rate of one scan/s. Individual charge states of the protein molecular ions were first isolated and then dissociated by electron capture dissociation (ECD) using 5-6% "electron energy" and a 150-250 ms duration time with no delay. Up to 1000 transients were averaged per spectrum to ensure high quality ECD spectra from low abundant precursor ions. For collisionally activated dissociation (CAD)[1] precursor ions were activated using 10-35% normalized collision energy at the default activation q of 0.25 and dissociated in the linear ion trap followed by detection in FTICR cell. All FTICR spectra were processed with Xtract Software (FT programs 2.0.1.0.6.1.4, Xcalibur 2.0.5, Thermo Scientific Inc., Bremen, Germany) using a signal-to-noise threshold of 1.5 and fit factor of 60% and validated manually. The resulting monoisotopic mass lists were further searched using in-house "ion-assignment" software.

II. Optimization of Enrichment Conditions to Minimize the Non-Specific Binding

We have sought to minimize non-specific binding to achieve the best enrichment by optimizing the buffers used in binding, washing, and eluting steps. For example, $ZrO_2$ has amphoteric properties as a result of unsatisfied valences of both oxygen and zirconium atoms on the surface layer so that it can act either as a Lewis acid or base depending on the pH of the reaction solution.[2] In acidic solutions, $ZrO_2$ behaves as a Lewis acid with positively charged Zr atoms displaying anion-exchange properties such as high binding affinity for phosphate, borate, carboxylate, and sulfate.[3] That high binding selectivity of phosphorylated peptides over nonphosphorylated acidic peptides can be achieved with proper selection of solution pH since the binding constant of phosphate ions is markedly higher than for other Lewis bases. As demonstrated by Hakansson and co-workers, high phosphopeptide binding selectivity was achieved at low pH solution (pH 2-3).[3] In addition, it has been found that phthalic acid can help prevent nonspecific binding.[4] For this work we chose 20 mg/mL phthalic acid in 0.1% TFA in 50/50 water/ACN (pH 2.0) as binding buffers. A comparison has been made between different binding, washing, and eluting buffers (See, FIG. 3). The abundant non-specific binding of unphosphorylated peptides is observed in FIG. 3b with pure water as the washing buffer and piperidine as the eluting buffer. Non-specific binding was clearly reduced in FIG. 3c, d by using 0.1% TFA, or 50 mM $NH_4HCO_3$, respectively, as the washing buffers and piperidine as the eluting buffer. The best results were achieved in FIG. 3f with the binding buffer of 20 mg/mL phthalic acid in 0.1% TFA in 50/50 water/ACN (pH 2.0), washing buffer of 50 mM $NH_4HCO_3$ in 50/50 water/ACN and eluting buffer of $NH_4OH$ (pH 11.5).

III. Identification of Phosphopeptides by Tandem Mass Spectrometry

Figure 6:
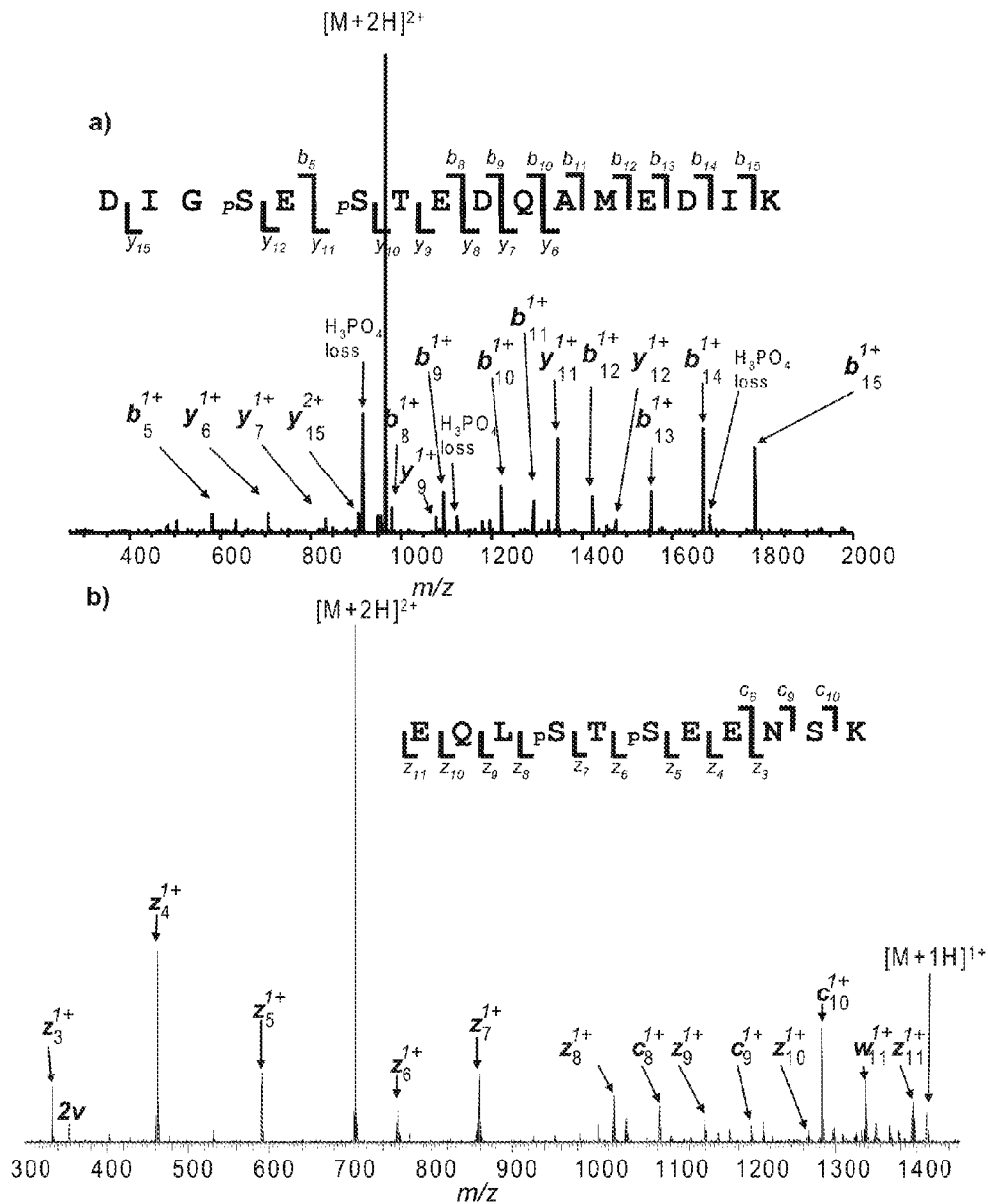
FIG. 6. Representative positive ion mode CAD (a) and ECD (b) spectra of phosphopeptides from an α-casein digest after mesoporous ZrO$_2$ enrichment. 2v corresponds to the second harmonic of the parent peak and W$_{11}$$^{1+}$ is resulted from side chain loss from the glutamic acid residue on the N-terminus.
Figure 7:
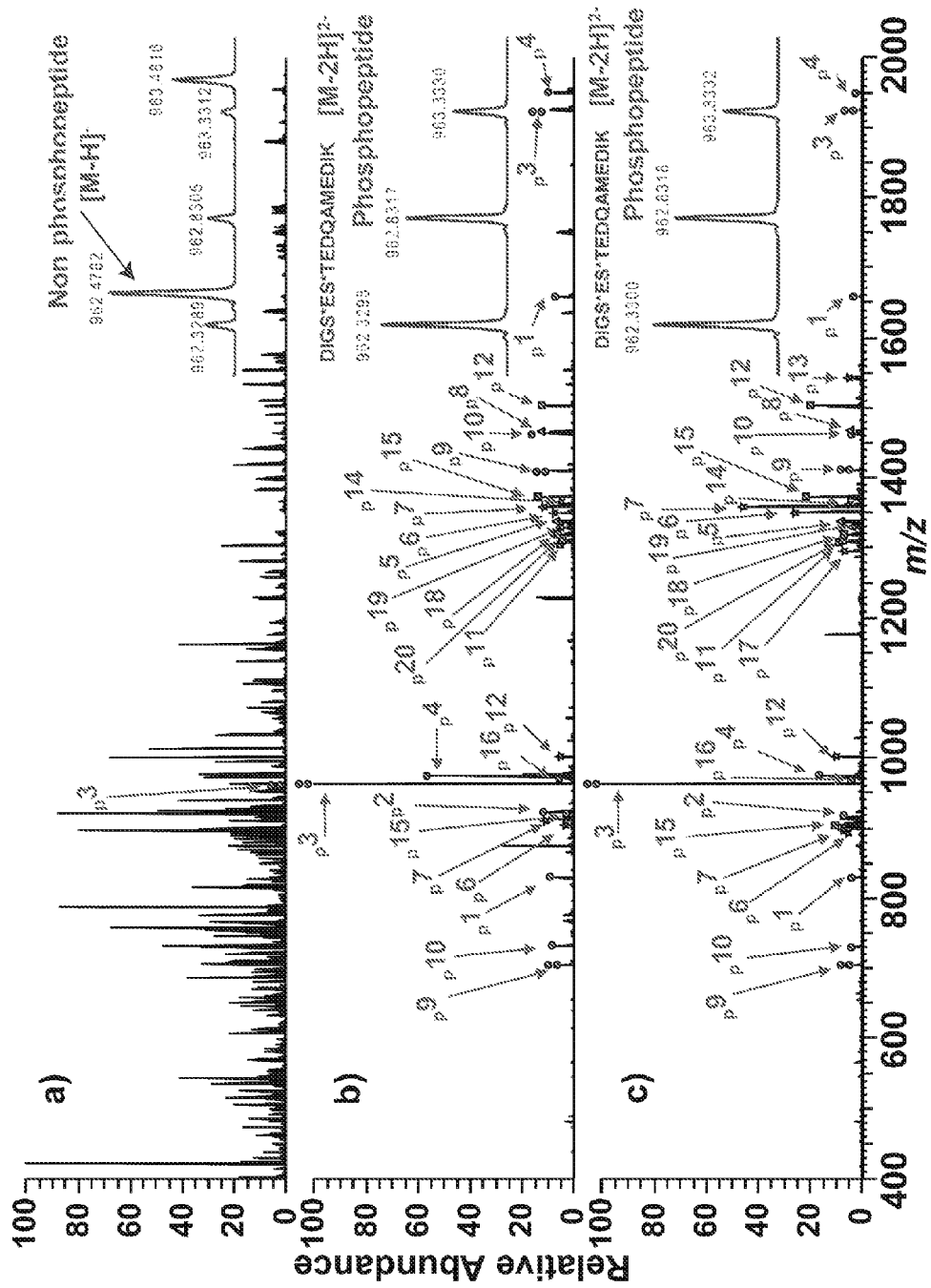
FIG. 7. Negative ion mode ESI/FTMS spectra of peptide mixtures digested from 6-protein mixture with trypsin acquired before enrichment (a), and after enrichment with mesoporous ZrO$_2$ (b) and HfO$_2$ (c). Circle, double circle, triangle, square, and star indicate singly, doubly, triply, quadruply and quintuply phosphorylated peptides, respectively. Phosphopeptides labeled with numbers are identified and shown in Table 3. Insets are expanded MS spectra at m/z 962-964; a singly charged non-phosphopeptide at m/z 962.47 in (a) and a doubly charged diphosphopeptide at m/z 962.33 in (b, c).

Phosphopeptides are identified in the CAD spectra based on the facile neutral loss of phosphoric acid ($H_3PO_4$) or metaphosphoric acid ($HPO_3$) from phosphorylated serine/threonine/tyrosine phosphopeptides in CAD MS/MS spectra. For example, CAD (MS/MS and $MS^3$) of a phosphopeptide in the negative ion mode (FIG. 5) shows consecutive loss of five phosphate groups which identified it as a quintuply phosphorylated peptide. The sequences of the detected phosphopeptides were further confirmed by high accuracy precursor masses and MS/MS (both CAD and ECD) acquired in high resolution FTICR mass spectrometer. Since the MS/MS dissociation efficiency in positive ion mode is much higher and its mechanism is better understood than that of peptide anions,[3] ECD and CAD spectra were taken primarily in positive ion mode to sequence and characterize phosphopeptides. The phosphopeptides detected in positive ion mode is comparable to those observed in negative ion mode (See, FIG. 11) although negative ionization is known to provide higher sensitivity for phosphopeptides than positive ionization.[3] Examples of CAD and ECD for localization of phosphorylation sites were shown in FIG. 6. CAD cleaves CO—NH bonds to produce b and y fragment ions.[1] CAD of the phosphopeptide DIGpSEpSTEDQAMEDIK was taken with 10% "collision energy" and was confirmed to be phosphorylated because of a 98 Da neutral loss from the precursor and fragment ions (See, FIG. 6a). ECD was employed to fully characterize phosphopeptides and localize the phosphorylation sites. ECD cleaves NH—CHR bonds to produce mainly c and z ions,[5] complementary to CAD. ECD is nonergodic,[5,6] known to preserve labile phosphorylation in peptides or intact proteins.[7,8] As shown in FIG. 6b, ECD was collected from a doubly charged precursor ion at m/z 706.2585 with 6% "electron energy" and an irradiation time of 250 msec. This yielded complete sequence coverage of the peptide EQLpSTp-SEENSK and the peptide was confirmed to be diphosphorylated at the two serine residues close to the N-terminus. Peaks in both CAD and ECD spectra were manually assigned with very high mass accuracy (<5 ppm) (See, Table 4 and 1). The list of phosphopeptides identified in FIGS. 4 and 7 is shown in Table 2. A previously reported peptide at 2702.8559 was found to match a different sequence that corresponds to a loss of ammonia from the N-terminal glutamine residue condensing to form pyroglutamate. In addition, a new variant of α-casein 51 (p16 in Table 2) was found and confirmed by MS/MS. This variant is an amino acid substitution on position 68 in α-casein 51 from Ala to Ser.

IV. Reuse of the Mesoporous Oxide Nanomaterials

Regeneration of the mesoporous materials was accomplished by combining all previously used materials into a single 1.5 mL centrifuge tube. The materials were washed with 1 mL of ACN and vortexed thoroughly for 5 minutes, centrifuged and the supernatant discarded. Then 1 mL of concentrated $NH_4OH$ was added and vortexed for 5 mins, centrifuged and the supernatant discarded. After the mesoporous materials were dried to completion, they were ready to be reused for phosphopeptide enrichment.

V. Comparison with Commercial Phosphoenrichment Product

Figure 11:
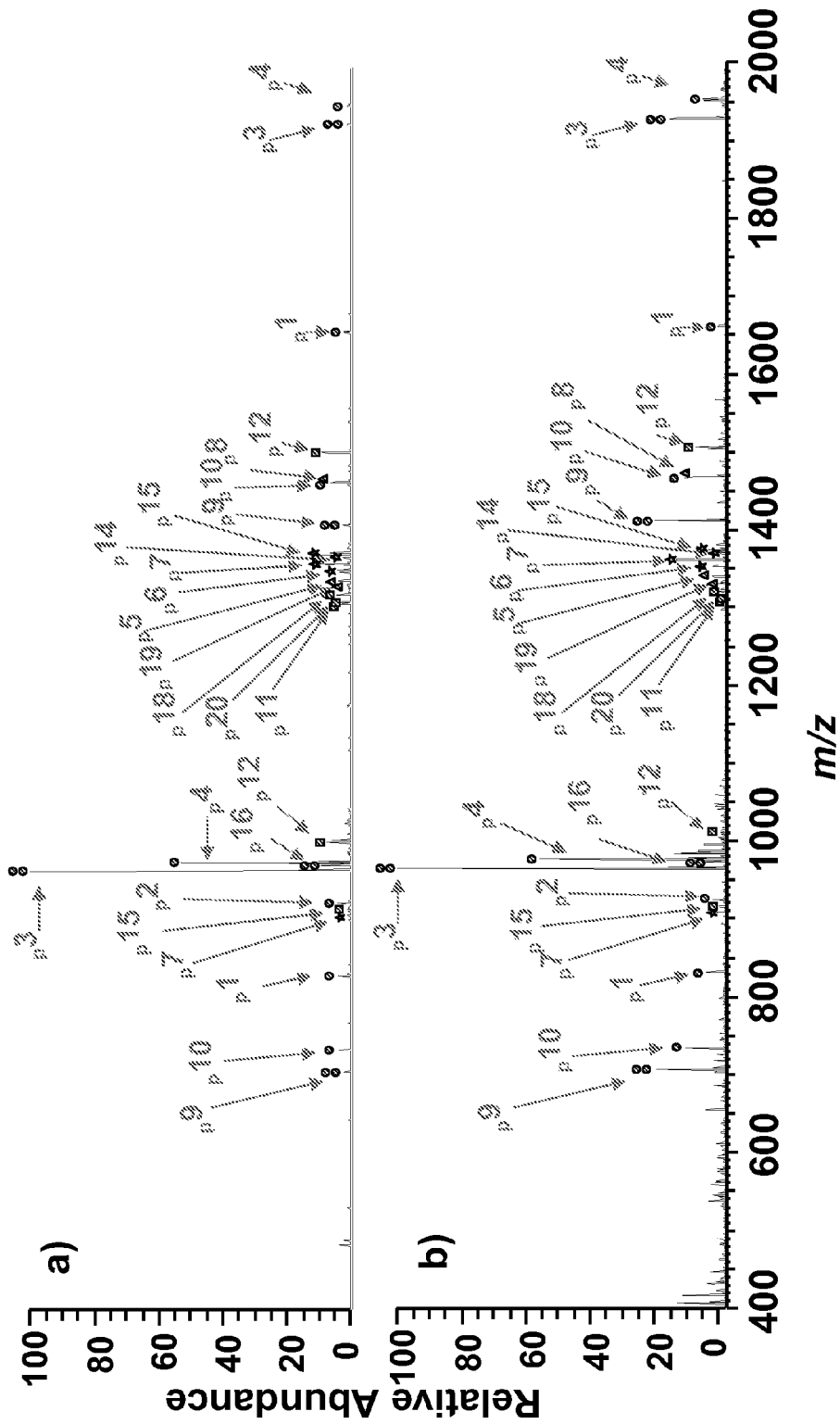
FIG. 11. Comparison of positive and negative ion mode ESI/FTMS spectra for phosphopeptide detection. (a) Negative ion mode and (b) Positive ion mode ESI/FTMS spectra of peptide mixtures digested from α-casein with trypsin after ZrO$_2$ enrichment. Circle, double circle, triangle, square, and star indicate singly-, doubly-, triply-, quadruply- and quintuply phosphorylated peptides, respectively. Phosphopeptides labeled with numbers are identified and shown in Table 3.

A side-by-side quantitative comparison of two leading commercially available phosphoenrichment products, one based on immobilized metal affinity chromatography (IMAC) technology (See, FIG. 10A) and the other of $ZrO_2$ packed tips (See, FIG. 10B), with the $ZrO_2$ mesoporous materials reported herein (See, FIG. 10C) has been performed. The morphology of the material used in $ZrO_2$ packed tips is shown as supplemental FIG. 6. We used the same quantity and concentration of the same tryptic digest of α-casein for the three enrichments (10 μL of tryptic digest from α-casein (4 pmol/μL). The enrichment experiments with the commercial products were performed according to manufacturers' instructions. Briefly, for the enrichment with the IMAC-based product, the spin column was washed with 50 μL supplied Bind/Wash Solution (250 mM acetic acid in 30% acetonitrile). The sample was added and incubated at room temperature for 15 minutes, then washed 3 times with 50 μL Bind/Wash Solution and once with 50 μL water to remove residual Bind/Wash solution. The phosphopeptides was eluted by centrifugation with Elution Solution (0.4 M ammonium hydroxide) and dried down in a speedvac to remove excessive ammonium hydroxide and reconstituted in 0.5% ammonium hydroxide. The enrichment with the commercial $ZrO_2$ packed tips was performed with Loading Buffer of 0.3% formic acid, Wash Buffer as Loading Buffer or water and Elution Buffer of ammonium hydroxide (pH 9.5-11). Tips were conditioned by aspirating the Loading Buffer 5 times. Then the tips were aspirated in air to remove excess Loading Buffer. Samples were aspirated/expelled 50 times to allow the peptides to adsorb to the $ZrO_2$ material, washed 10 times with 20 μL of Wash Buffer and eluted with the Elution Buffer (0.5% ammonium hydroxide). The enrichment with our mesoporous $ZrO_2$ product uses a binding solution of 20 mg/mL in 0.1% TFA 50/50 $H_2O$/ACN, a wash buffer of 50 mM $NH_4HCO_3$ in 50/50 ACN/$H_2O$ and an elution buffer of 0.5% $NH_4OH$. As shown in FIG. 11, the mesoporous $ZrO_2$ materials showed significantly higher efficiency and specificity for phosphopeptide enrichment over these two leading commercial products. After enrichment with the IMAC-based enrichment product (See, FIG. 10A), 7 multiply charged MS peaks corresponding to 7 phosphopeptides were identified in one MS spectrum. Nevertheless, it suffers from severe non-specific binding of potentially acidic peptides since many highly abundant non-phosphopeptides still dominate the spectrum. Enrichment with the $ZrO_2$ packed tips (See, FIG. 10B) revealed 6 multiply charged MS peaks corresponding to 6 phosphopeptides in one MS spectrum. In contrast, an enrichment with our mesoporous $ZrO_2$ nanomaterials detected 27 multiply-charged MS peaks corresponding to 19 phosphopeptides (See, FIG. 10C), which demonstrated significantly higher efficiency and unparalleled specificity for phosphopeptides as nearly all the non-specific bindings were suppressed.

VI. The Nanoparticle Morphology of the $Zro_2$-Based Commercial

Figure 12:
FIG. 12. Representative scanning electron microscope (SEM) images of the commercial phosphoenrichment materials based on ZrO$_2$, which consist of microspheres of aggregates of ZrO$_2$ nanoparticles of about 20 nm diameter. This was the materials used for enrichment experiment shown in FIG. 10B FIG. 13 provides a schematic drawing of the mesoporous metal oxide packed tip for phospho-enrichment that was evaluated. Specifically.

Phosphoenrichment Product. FIG. 12 provides representative SEM images of the commercial phosphoenrichment materials based on $ZrO_2$, which consist of microspheres of aggregates of $ZrO_2$ nanoparticles of about 20 nm diameter. This was the materials used for enrichment experiment shown in FIG. 10B.

REFERENCES

[1] M. W. Senko, J. P. Speir, F. W. McLafferty, *Anal. Chem.* 1994, 66, 2801-2808.
[2] J. Nawrocki, J. Rigney, A. McCormick, P. W. Carr, *J. Chromatogr. A* 1993, 657, 229-282.
[3] H. K. Kweon, K. Hakansson, *Anal. Chem.* 2006, 78, 1743-1749.
[4] T. E. Thingholm, T. J. D. Jorgensen, O. N. Jensen, M. R. Larsen, *Nat. Protocols* 2006, 1, 1929-1935.

[5] R. A. Zubarev, D. M. Horn, E. K. Fridriksson, N. L. Kelleher, N. A. Kruger, M. A. Lewis, B. K. Carpenter, F. W. McLafferty, *Anal. Chem.* 2000, 72, 563-573.

[6] R. A. Zubarev, N. L. Kelleher, F. W. McLafferty, *J. Am. Chem. Soc.* 1998, 120, 3265-3266.

[7] S. D. H. Shi, M. E. Hemling, S. A. Carr, D. M. Horn, I. Lindh, F. W. McLafferty, *Anal. Chem.* 2001, 73, 19-22.

[8] H. J. Cooper, K. Hakansson, A. G. Marshall, *Mass Spectrom. Reviews* 2005, 24, 201-222.

TABLE 1

Fragment ion assignments for CAD spectrum of phosphopeptides from an α-casein digest after mesoporous $ZrO_2$ enrichment as shown in FIG. 6, top.

| fragment type | Expt'l mass | Calc'd mass | Mass error (Da) | Mass error (ppm) |
|---|---|---|---|---|
| $b_5$ | 581.1739 | 581.1734 | −0.00052 | 0.89 |
| $b_8$ | 978.2620 | 978.2620 | −2E−05 | 0.020 |
| $b_9$ | 1093.2891 | 1093.2889 | −0.00018 | 0.16 |
| $b_{10}$ | 1221.3497 | 1221.3475 | −0.0022 | 1.8 |
| $b_{11}$ | 1292.3863 | 1292.3846 | −0.0017 | 1.3 |
| $b_{12}$ | 1423.4265 | 1423.4251 | −0.0014 | 0.98 |
| $b_{13}$ | 1552.4702 | 1552.4677 | −0.0025 | 1.6 |
| $b_{14}$ | 1667.4963 | 1667.4946 | −0.0017 | 1.0 |
| $b_{15}$ | 1780.5809 | 1780.5787 | −0.0022 | 1.2 |
| $y_7$ | 833.3957 | 833.3953 | −0.00041 | 0.49 |
| $y_8$ | 948.4233 | 948.4222 | −0.0011 | 1.1 |
| $y_{11}$ | 1345.5124 | 1345.5108 | −0.0016 | 1.2 |
| $y_{12}$ | 1474.5548 | 1474.5534 | −0.0014 | 0.94 |
| $y_{16}$ | 1926.6853 | 1926.6842 | −0.0011 | 0.56 |
| $b_{10}$-$H_3PO_4$ | 1682.603 | 1682.6041 | 0.0011 | −0.65 |
| $b_{15}$-$H_3PO_4$ | 1828.709 | 1828.7071 | −0.0019 | −0.65 |

TABLE 2

Fragment assignments for ECD spectrum of phosphopeptide from an α-casein digest after mesoporous $ZrO_2$ enrichment as shown in FIG. 6, bottom.

| fragment type | Expt'l mass | Calc'd mass | Mass error (Da) | Mass error (ppm) |
|---|---|---|---|---|
| $z'_3$ | 332.1684 | 332.1690 | −0.00064 | −1.9 |
| $z'_4$ | 461.2108 | 461.2116 | −0.00083 | −1.8 |
| $z'_5$ | 590.2528 | 590.2542 | −0.0014 | −2.4 |
| $z'_6$ | 757.2508 | 757.2526 | −0.0018 | −2.3 |
| $z'_7$ | 858.3016 | 858.3002 | 0.0014 | 1.6 |
| $z'_8$ | 1025.2965 | 1025.2986 | −0.0021 | −2.0 |
| $z^\bullet_5$ | 589.245 | 589.2469 | −0.0019 | −3.3 |
| $z^\bullet_9$ | 1137.3745 | 1137.3753 | −0.00084 | −0.74 |
| $z^\bullet_{10}$ | 1265.4342 | 1265.4339 | 0.00028 | 0.22 |
| $z^\bullet_{11}$ | 1394.475 | 1394.4765 | −0.0015 | −1.1 |
| $c_8$ | 1080.3379 | 1080.3413 | −0.0034 | −3.1 |
| $c_9$ | 1194.3786 | 1194.3842 | −0.0056 | −4.7 |
| $c_{10}$ | 1281.4133 | 1281.4162 | −0.003 | −2.3 |
| $w_{11}$ | 1335.4604 | 1335.4637 | −0.0033 | −2.5 |

TABLE 3

List of phosphopeptide identified in the negative ion mode FTMS spectra (FIG. 4 and 7) of peptide mixtures digested from α-casein with trypsin acquired before enrichment (a), after enrichment with mesoporous $ZrO_2$ (b) and $HfO_2$ (c).

| Peptide # | Expt'l (m/z) | Charge State | Expt'l Mass | Calc'd Mass | Error (ppm) | Sequence Identified | Phosphorylation state | Assignment |
|---|---|---|---|---|---|---|---|---|
| $_p1$ | 828.8824 | −2 | 1659.7759 | 1659.7869 | −6.6 | VPQLEIVPNS*AEER | 1 | α-S1[121-134][b] |
| | 1658.7689 | −1 | 1659.7779 | 1659.7869 | −5.4 | VPQLEIVPNS*AEER | 1 | α-S1[121-134][a,b] |
| $_p2$ | 922.3468 | −2 | 1846.7159 | 1846.7179 | −1.1 | DIGS*ESTEDQAMEDIK | 1 | α-S1[58-73][b] |
| $_p3$ | 962.3299 | −2 | 1926.6759 | 1926.6842 | −4.3 | DIGS*ES*TEDQAMEDIK | 2 | α-S1[58-73][a,b] |
| | 1925.6644 | −1 | 1926.6679 | 1926.6842 | 8.5 | DIGS*ES*TEDQAMEDIK | 2 | α-S1[58-73][a,b] |
| $_p4$ | 974.462 | −2 | 1950.9359 | 1950.9451 | −4.7 | YKVPQLEIVPNS*AEER | 1 | α-S1[119-134][a,b] |
| | 1949.9218 | −1 | 1950.9279 | 1950.9451 | −8.8 | YKVPQLEIVPNS*AEER | 1 | α-S1[119-134][a,b] |
| $_p5$ | 1337.4917 | −2 | 2676.9959 | 2677.0115 | −7.3 | VNELS*KDIGS*ES*TEDQAMEDIK | 3 | α-S1[52-73][b] |
| $_p6$ | 899.9485 | −3 | 2702.8673 | 2702.8626 | 1.8 | pyroQMEAES*IS*S*S*EEIVPNS*VEQK[1] | 5 | α-S1[114-135][b] |
| | 1350.423 | −2 | 2702.8559 | 2702.8626 | 2.5 | pyroQMEAES*IS*S*S*EEIVPNS*VEQK[1] | 5 | α-S1[114-135][a,b] |
| $_p7$ | 905.6242 | −3 | 2719.8839 | 2719.9055 | −7.9 | QMEAES*IS*S*S*EEIVPNS*VEQK | 5 | α-S1[74-94][b] |
| | 1358.9367 | −2 | 2719.8959 | 2719.9055 | −3.5 | QMEAES*IS*S*S*EEIVPNS*VEQK | 5 | α-S1[74-94][b] |
| $_p8$ | 1466.06 | −2 | 2934.1359 | 2934.1530 | −5.8 | EKVNELS*KDIGS*ES*TEDQAMEDIK | 3 | α-S1[50-73][b] |
| $_p9$ | 704.2372 | −2 | 1410.4959 | 1410.4952 | 0.47 | EQLS*TS*EENSK | 2 | α-S2[141-151][a,b] |
| | 1409.4785 | −1 | 1410.4879 | 1410.4952 | −5.2 | EQLS*TS*EENSK | 2 | α-S2[141-151][b] |
| $_p10$ | 731.792 | −2 | 1465.5959 | 1465.6047 | −6.0 | TVDMES*TEVFTK | 1 | α-S2[153-164][b] |
| | 1464.5881 | −1 | 1465.5979 | 1465.6047 | −4.7 | TVDMES*TEVFTK | 1 | α-S2[153-164][b] |
| $_p11$ | 1307.9331 | −2 | 2617.8801 | 2617.8879 | −2.3 | NTMEHVS*S*S*EESIIS*QETYK | 4 | α-S2[17-36][b] |
| $_p12$ | 1001.3274 | −3 | 3007.0139 | 3007.0221 | −2.7 | NANEEEYSIGS*S*S*EES*AEVATEEVK | 4 | α-S2[61-85][b] |
| | 1502.4936 | −2 | 3006.9959 | 3007.0221 | −8.7 | NANEEEYSIGS*S*S*EES*AEVATEEVK | 4 | α-S2[61-85][b] |
| $_p14$ | 1366.9350 | −2 | 2735.8847 | 2735.9004 | −5.8 | QMEAES*IS*S*S*EEIVPNS*VEQK[2] | 5 | α-s1[74-94][b] |
| $_p15$ | 914.32 | −3 | 2745.9839 | 2745.9923 | −3.1 | NTMEHVS*S*S*EESIIS*QETYKQ | 4 | α-S2[17-37][b] |
| | 1371.9798 | −2 | 2745.9742 | 2745.9559 | 6.6 | NTMEHVS*S*S*EESIIS*QETYKQ | 4 | α-S2[17-37][a,b] |
| $_p16$ | 970.3289 | −2 | 1942.6724 | 1942.6791 | −3.0 | DIGS*ES*TEDQSMEDIK | 2 | α-S2[58-73][b] |
| $_p17$ | 1294.9093 | −2 | 2591.8332 | 2591.8332 | 8.7 | QMEAES*IS*S*S*EEIVPNS*VEQ | 5 | α-S1[74-93][b] |
| $_p18$ | 1318.9558 | −2 | 2639.9262 | 2639.9392 | −4.9 | QMEAES*IS*S*S*EEIVPNSVEQK | 4 | α-S1[74-94][b] |
| $_p19$ | 1331.9985 | −2 | 2666.0116 | 2665.9896 | 8.2 | NTMEHVS*S*S*EESIISQETYKQ | 3 | α-S2[17-36][b] |
| $_p20$ | 1310.4443 | −2 | 2622.9032 | 2622.8833 | 7.6 | pyroQMEAES*IS*S*S*EEIVPNSVEQK | 4 | α-S1[74-94][b] |
| $_p21$ | 768.2900 | −2 | 1538.5945 | 1538.5902 | 2.8 | EQLS*TS*EENSKK | 2 | α-S2[141-152][b] |
| $_p22$ | 795.8395 | −2 | 1593.6935 | 1593.6997 | 3.9 | TVDMES*TEVFTKK | 1 | α-S2[153-165][b] |

[1]This sequence corresponds to a loss of ammonia from the N-terminal glutamine residue condensing to form pyroglutamate.
[2]M represents oxidized methionine

TABLE 4

Final protein concentrations and the quantity (moles) present in 100 μL of the 6-protein mixture used for enrichment.

|  | BSA | β-Lactoglobulin | Ubi | RNase B | Troponin C[1] | α-casein |
|---|---|---|---|---|---|---|
| Average Molecular Weight (kDa) | 69.2 | 19.9 | 8.6 | 15 | 18 | 25.2 |
| Concentration (μg/μL) | 0.2 | 0.02 | 0.02 | 0.02 | 0.02 | 0.02 |
| Concentration (pmol/μL) | 2.9 | 1 | 2 | 1 | 1 | 0.8 |
| Protein quantity (mole) | 3E−10 | 1E−10 | 2E−10 | 1E−10 | 1E−10 | 8E−11 |

[1]Troponin C is the major component (95%) of porcine troponin purchased from Sigma suggested by ESI/FTMS and SDS-PAGE analysis of the intact proteins.

EXAMPLE 2

Mesoporous Metal Oxide Packed Tip for Phospho-Enrichment

Figure 13:
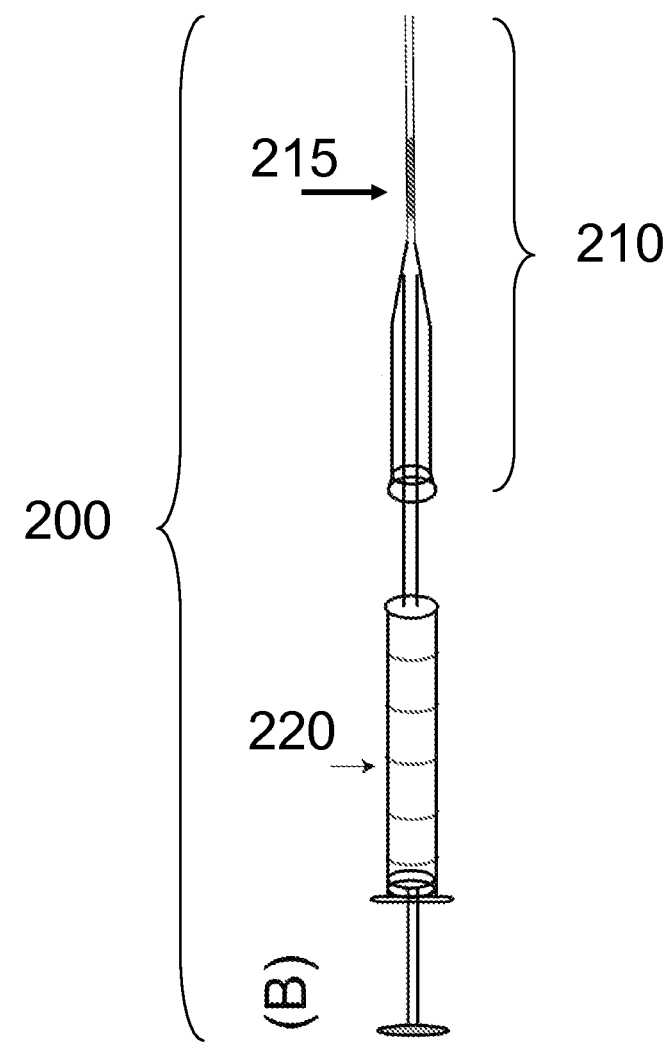
FIG. 13A illustrates an in-house developed phosphoenrichment product with a gel-loading tip packed with mesoporous metal oxides and FIG. 13B illustrates a packed tip coupled with an offline syringe pump.
Figure 13:
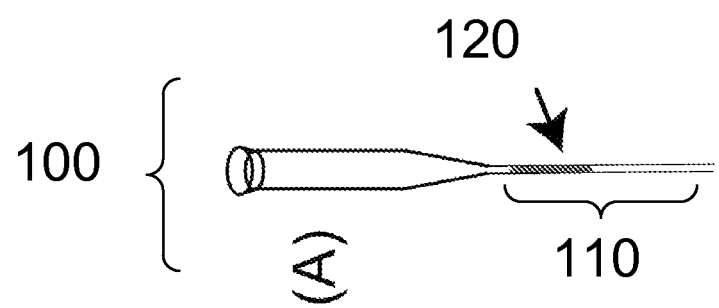

This Example provides a description pertaining to the development of a phosphoenrichment tool provided in a packed tip format using a gel-loading tip packed with a mesoporous metal oxide enrichment material. FIG. 13 provides a schematic drawing of the mesoporous metal oxide packed tip for phospho-enrichment. Specifically, FIG. 13A illustrates an in-house developed packet-tip phosphoenrichment product (100) with a gel-loading tip (110) packed with mesoporous metal oxides (120), such as mesoporous $ZrO_2$ and/or $HfO_2$ beads. FIG. 13B illustrates a packet-tip phosphoenrichment product (200) comprising a packed gel tip (210) packed with mesoporous metal oxides (215) such as mesoporous $ZrO_2$ and/or $HfO_2$ beads, wherein the tip is coupled with an offline syringe pump (220) to provide a flow of sample through the packed gel tip (210). The packed tip is easily coupled with an offline syringe pump for enrichment applications, which can be coupled on-line with HPLC/MS as well.

Figure 14:
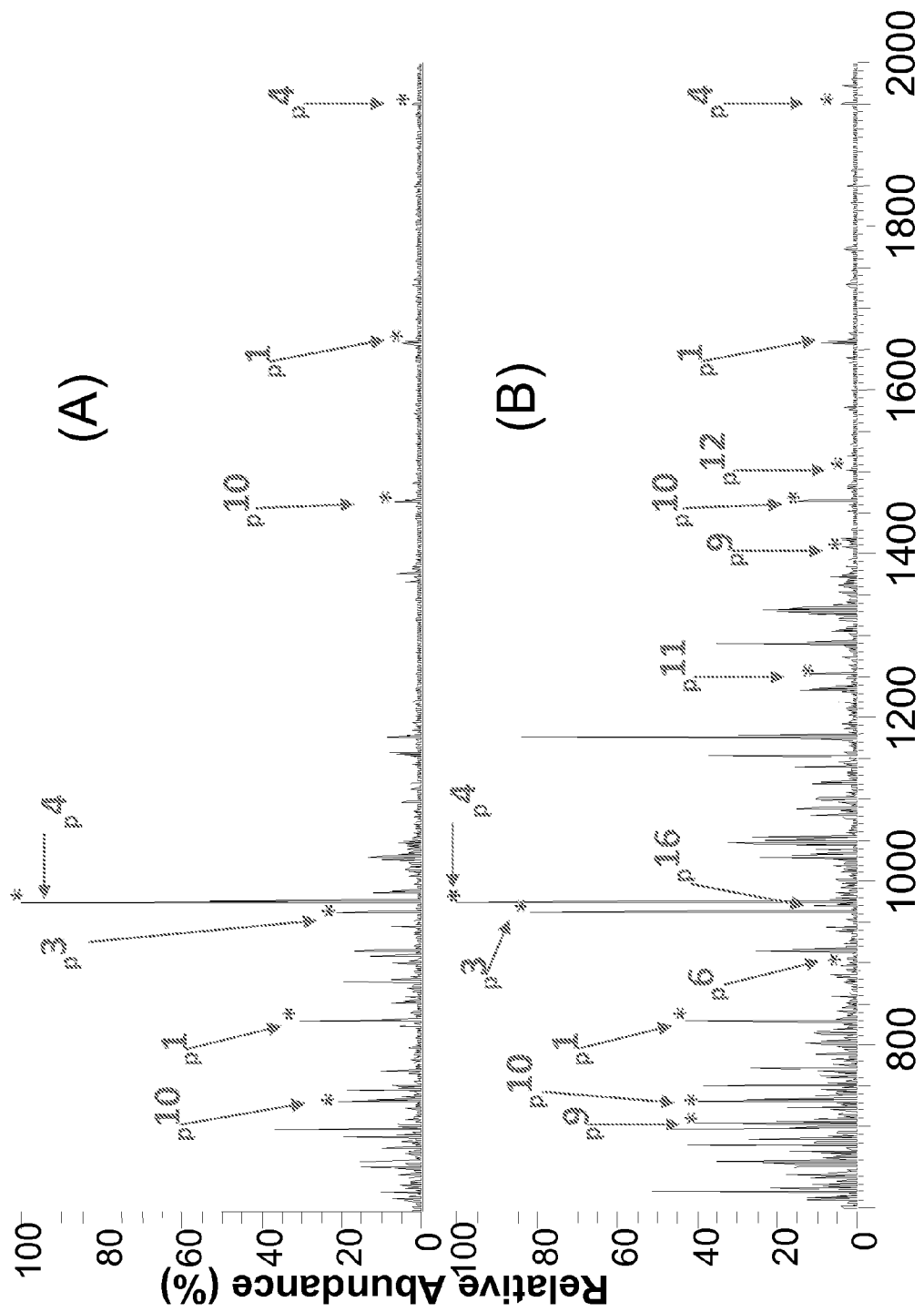
FIG. 14 provides experimental results for enrichment of phosphopeptides achieved using the packed tip. Specifically, this figure provides mass spectra of samples of trypsin digested α-casein enriched using a ZrO$_2$ packed tip (FIG. 14A) and a HfO$_2$ packed tip (FIG. 14B).

FIG. 14 provides experimental results for enrichment of phosphopetides achieved using the packed tip. Specifically, this figure provides mass spectra of samples of trypsin digested α-casein enriched using a $ZrO_2$ packed tip (FIG. 14A) and a $HfO_2$ packed tip (FIG. 14B). As shown in Panel A of FIG. 14, enrichment using the mesoporous $ZrO_2$ packed tip yielded 7 multiply charged MS peaks corresponding to 4 phosphopeptides identified in a single mass spectrum. As shown in Panel B of FIG. 14, enrichment with $HfO_2$ packed tip yielded 13 multiply charged MS peaks corresponding to 8 phosphopeptides. The observation of nonspecific binding, shown in FIG. 14, is likely due to the omission of phthalic acid in the binding solution, an agent that enhances specific binding. Due to the difference between our previous spin-column format and the current packed tip format, further optimization in the enrichment buffers, the loading speeds and other parameters is likely to result in higher yields.

In an embodiment, the present invention provides an enrichment device for enriching phosphorylated compounds in a sample; said device comprising: (1) a packed gel tip packed with an enrichment material comprising a metal oxide mesoporous material, and (2) a syringe pump or other fluidic driving pump for creating a flow of said sample through said packed tip; wherein upon generating said flow of sample through the packed tip, at least a portion of said phosphorylated compounds selectively bind to the metal oxide mesoporous material. As will be understood by one having skill in the art, the methods described above, and the variations thereof disclosed, may be carried out using the disclosed enrichment device.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention.

Whenever a range is given in the specification, for example, a range of integers, a temperature range, a time range, or a composition range, or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for enriching phosphorylated compounds in a sample, said method comprising the steps of:
    providing said sample containing the phosphorylated compounds;
    contacting said sample with an enrichment material comprising a metal oxide mesoporous material generated via controlled hydrolysis of metal salts templated using nanoscale micellular structures, said metal oxide mesoporous material having a plurality of pores with cross sectional dimensions selected over the range of 2 to 50 nm provided in a well ordered hexagonal or cubic bicontinuous network, thereby providing an active area of exposed surfaces greater than or equal to 50 $m^2\ g^{-1}$;
    wherein at least a portion of said phosphorylated compounds selectively binds to the metal oxide mesoporous material;
    separating said phosphorylated compounds bound to the metal oxide mesoporous material from at least a portion of the sample; and
    releasing the phosphorylated compounds bound to the metal oxide mesoporous material from the metal oxide mesoporous material, thereby enriching said phosphorylated compounds in the sample.

2. The method of claim 1 wherein said enrichment material comprises one or more metal oxide selected from the group consisting of $ZrO_2$, $HfO_2$, $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, $Zr_xHf_{1-x}O_2$ wherein 0<x<1, $Zr_xTi_{1-x}O_2$ wherein 0<x<1, $Ti_xHf_{1-x}O_2$ wherein 0<x<1, and $(Fe_{1-x}Ga_x)_2O_3$ wherein 0<x<1.

3. The method of claim 1 wherein said enrichment material comprises mesoporous $ZrO_2$ or $HfO_2$.

4. The method of claim 1 wherein said contacting step comprises adding said enrichment material to said sample; wherein the amount of said enrichment material added is selected over the range of 0.001 g to 100 g per milliliter of sample.

5. The method of claim 1 wherein said contacting step is carried out at a pH selected over the range of 1.5 to 4.0.

6. The method of claim 1 wherein said contacting step is carried out in a solution having an ionic strength selected over the range of 0.01 M to 0.05M.

7. The method of claim 1 wherein said separating step is carried out at a pH selected over the range of 5 to 11.

8. The method of claim 1 wherein said separating step further comprises eluting said sample contacted with said metal oxide mesoporous material having said bound phosphorylated compounds or washing said metal oxide mesoporous material having said bound phosphorylated compounds.

9. The method of claim 1 wherein said releasing step is carried out at a pH selected over the range of 10 to 13.

10. The method of claim 1 wherein said releasing step is carried out in a solution having an ionic strength selected over the range of 0.01 M to 0.05M.

11. The method of claim 1 further comprising the step of analyzing said phosphorylated compounds using mass spectrometry.

12. The method of claim 1 wherein said enrichment material comprises a metal oxide mesoporous material having an active area of exposed surfaces that are not chemically modified.

13. The method of claim 1 wherein said enrichment material comprises a metal oxide mesoporous material having an active area of exposed surfaces that are not functionalized with diazo group substituted organic moieties.

14. The method of claim 1 wherein said enrichment material comprises a metal oxide mesoporous material provided as an affinity column, a monolithic column, a minicolumn, a filter disk or a pipet tip.

15. The method of claim 1 wherein at least a portion of said phosphorylated compounds directly binds to the metal oxide mesoporous material.

16. The method of claim 1 further comprising the step of regenerating the enrichment material after said step of releasing the phosphorylated compounds bound to the metal oxide mesoporous material by exposing said enrichment material to a pH greater than or equal to 11.

17. The method of claim 1 wherein said enrichment material comprises a metal oxide mesoporous material having a surface area selected over the range 50 to 1000 $m^2$ per gram.

18. The method of claim 1 wherein said enrichment material comprises particles of said metal oxide mesoporous material having cross sectional dimensions ranging from 50 nanometers to 2 millimeters.

19. The method of claim 1 wherein said phosphorylated compounds are one or more phosphorylated peptides, phosphorylated proteins or both.

20. The method of claim 19 wherein said enrichment material comprises a mesoporous metal oxide that reversibly binds with said phosphorylated peptides, phosphorylated proteins or both.

21. A method for enriching phosphorylated peptides or proteins in a sample, said method comprising the steps of:
providing said sample containing the phosphorylated peptides or proteins;
contacting said sample with an enrichment material comprising a metal oxide mesoporous material generated via controlled hydrolysis of metal salts templated using nanoscale micellular structures, said metal oxide mesoporous material having a plurality of pores with cross sectional dimensions selected over the range of 2 to 50 nm provided in a well ordered hexagonal or cubic bicontinuous network, thereby providing an active area of exposed surfaces greater than or equal to 50 m$^2$ g$^{-1}$; wherein at least a portion of said phosphorylated peptides or proteins selectively binds to the metal oxide mesoporous material, said metal oxide selected from the group consisting of $ZrO_2$, $HfO_2$, $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, $Zr_xHf_{1-x}O_2$ wherein 0<x<1, $Zr_xTi_{1-x}O_2$ wherein 0<x<1, $Ti_xHf_{1-x}O_2$ wherein 0<x<1, and $(Fe_{1-x}Ga_x)_2O_3$ wherein 0<x<1;
separating said phosphorylated peptides or proteins bound to the metal oxide mesoporous material from at least a portion of the sample; and
releasing the phosphorylated peptides or proteins bound to the metal oxide mesoporous material from the metal oxide mesoporous material, thereby enriching said phosphorylated peptides or proteins in said sample.

22. The method of claim 21 further comprising digesting said sample prior to said step of contacting said sample with the enrichment material comprising the metal oxide mesoporous material.

23. The method of claim 21 wherein said contacting step is carried out at a pH selected from the range of 1.5- 5.0 and wherein said releasing step is carried out at a pH selected from the range of 10-13.

24. A method of analyzing phosphorylated proteins in a sample; said method comprising:
digesting said sample containing said phosphorylated proteins; thereby generating a solution containing phosphorylated peptides;
contacting said solution containing the phosphorylated peptides with an enrichment material comprising a metal oxide mesoporous material generated via controlled hydrolysis of metal salts templated using nanoscale micellular structures, said metal oxide mesoporous material having a plurality of pores with cross sectional dimensions selected over the range of 2 to 50 nm provided in a well ordered hexagonal or cubic bicontinuous network, thereby providing an active area of exposed surfaces greater than or equal to 50 m$^2$ g$^{-1}$; wherein at least a portion of said phosphorylated peptides selectively binds to the metal oxide mesoporous material, said metal oxide selected from the group consisting of $ZrO_2$, $HfO_2$, $TiO_2$, $Ga_2O_3$, $Cr_2O_3$, $Fe_2O_3$, $Fe_3O_4$, $Al_2O_3$, $La_2O_3$, $CeO_2$, $SnO_2$, $Ta_2O_5$, $Zr_xHf_{1-x}O_2$ wherein 0<x<1, $Zr_xTi_{1-x}O_2$ wherein 0<x<1, $Ti_xHf_{1-x}O_2$ wherein 0<x<1, and $(Fe_{1-x}Ga_x)_2O_3$ wherein 0<x<1;
separating said phosphorylated peptides bound to the metal oxide mesoporous material from at least a portion of the solution containing the phosphorylated peptides;
releasing the phosphorylated peptides bound to the metal oxide mesoporous material from the metal oxide mesoporous material, thereby generating a sample enriched in said phosphorylated peptides; and
analyzing said phosphorylated peptides of said sample enriched in said phosphorylated peptides using a mass spectrometry technique; thereby analyzing the phosphorylated proteins in said sample.

* * * * *